US008753880B2

(12) United States Patent
DeLouise et al.

(10) Patent No.: US 8,753,880 B2
(45) Date of Patent: Jun. 17, 2014

(54) METHOD OF ENRICHING STEM AND/OR PROGENITOR CELLS

(75) Inventors: Lisa DeLouise, Rochester, NY (US); Siddarth Chandrasekaran, Ithaca, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 13/544,555

(22) Filed: Jul. 9, 2012

(65) Prior Publication Data
US 2013/0012413 A1     Jan. 10, 2013

Related U.S. Application Data

(60) Provisional application No. 61/505,881, filed on Jul. 8, 2011.

(51) Int. Cl.
*C12M 3/00* (2006.01)
*C12N 5/095* (2010.01)
*C12M 1/32* (2006.01)

(52) U.S. Cl.
CPC .......... *C12N 5/0695* (2013.01); *C12N 2539/10* (2013.01); *C12M 23/12* (2013.01)
USPC ........................ 435/325; 435/372.3; 435/395

(58) Field of Classification Search
None
See application file for complete search history.

(56) References Cited

U.S. PATENT DOCUMENTS

2007/0190646 A1*  8/2007  Engler et al. .................. 435/325

OTHER PUBLICATIONS

Darling, E.M. et al. Mechanical Properties and Gene Expression of Chondrocytes on Micropatterned Substrates following Dedifferentiation in Monolayer.2009.Cellular and Molecular Bioengineering, 2(3):395-404. specif. pp. 395, 399-400.*
Hammerick, K.E. et al. Elastic Properties of Induced Pluripotent Stem Cells.2011.(First published online Oct. 15, 2010).Tissue Engineering: Part A, 17(3 and 4):495-502. specif. pp. 498, 500.*
Hirschhaeuser. F. et al. 2010. Multicellular tumor spheroids: An underestimated tool is catching up again. Journal of Biotechnology 148: 3-15. specif. pp. 6, 11.*
Chandrasekaran et al., "Microenvironment Induced Spheroid to Sheeting Transition of Immortalized Human Keratinocytes (HaCaT) Cultured in Microbubbles Formed in Polydimethylsiloxane," Biomat. 32(29):7159e68 (2011).
Na et al., "Isolation and Characterization of Spheroid Cells from Human Malignant Melanoma Cell Line WM-266-4," Tumour Biol. 30(5e6):300e9 (2009).
Agastin et al., "Continuously Perfused Microbubble Array for 3D Tumor Spheroid Model," Biomicrofluidics 5(2):024110 (2011).
Giang et al., "Microfabrication of Bubbular Cavities in PDMS for Cell Sorting and Microcell Culture Applications," J. Bionic Eng. 5:308-316 (2008).

* cited by examiner

*Primary Examiner* — John S Brusca
*Assistant Examiner* — Sharon M Papciak
(74) *Attorney, Agent, or Firm* — LeClairRyan, a Professional Corporation

(57) ABSTRACT

A method of enriching stem or progenitor cells that includes growing a heterogeneous cell sample comprising stem and/or progenitor cells on a first substrate that is hydrophobic and has an elastic modulus less than about 100 MPa; recovering the heterogeneous cell sample from the first substrate; growing the recovered heterogeneous cell sample on a second substrate that is hydrophilic and has an elastic modulus higher than the elastic modulus of the first substrate to produce a subpopulation of nonadherent cells and a subpopulation of adherent cells; and recovering the nonadherent cell subpopulation, which is enriched for stem and/or progenitor cells.

12 Claims, 12 Drawing Sheets

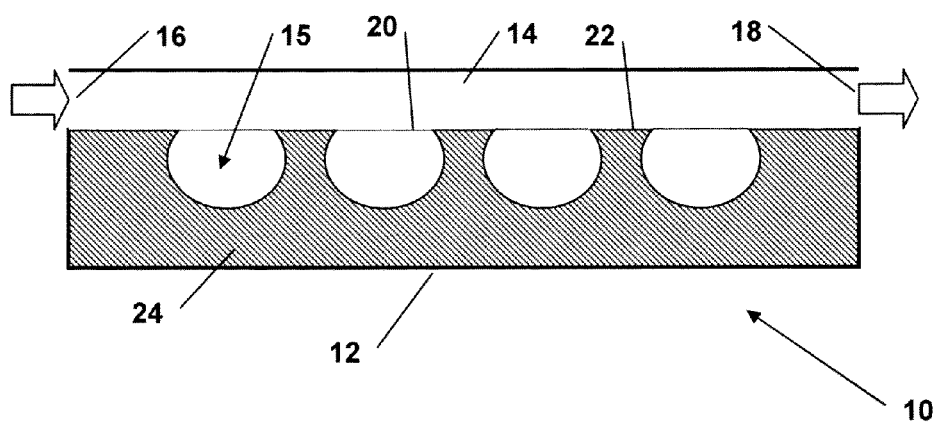
FIG. 2
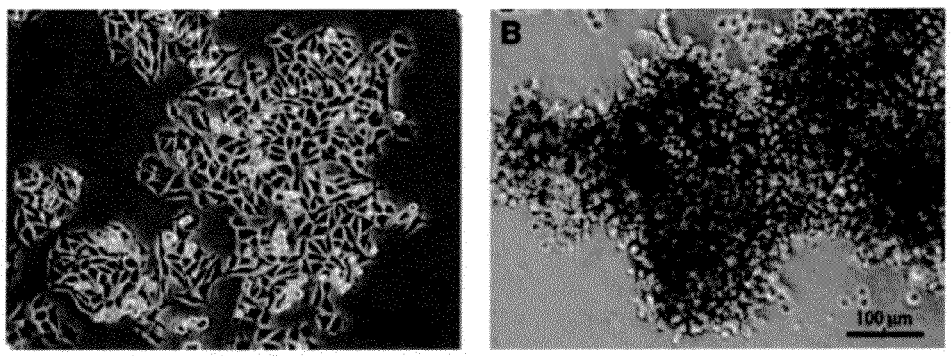
FIGS. 3A-B

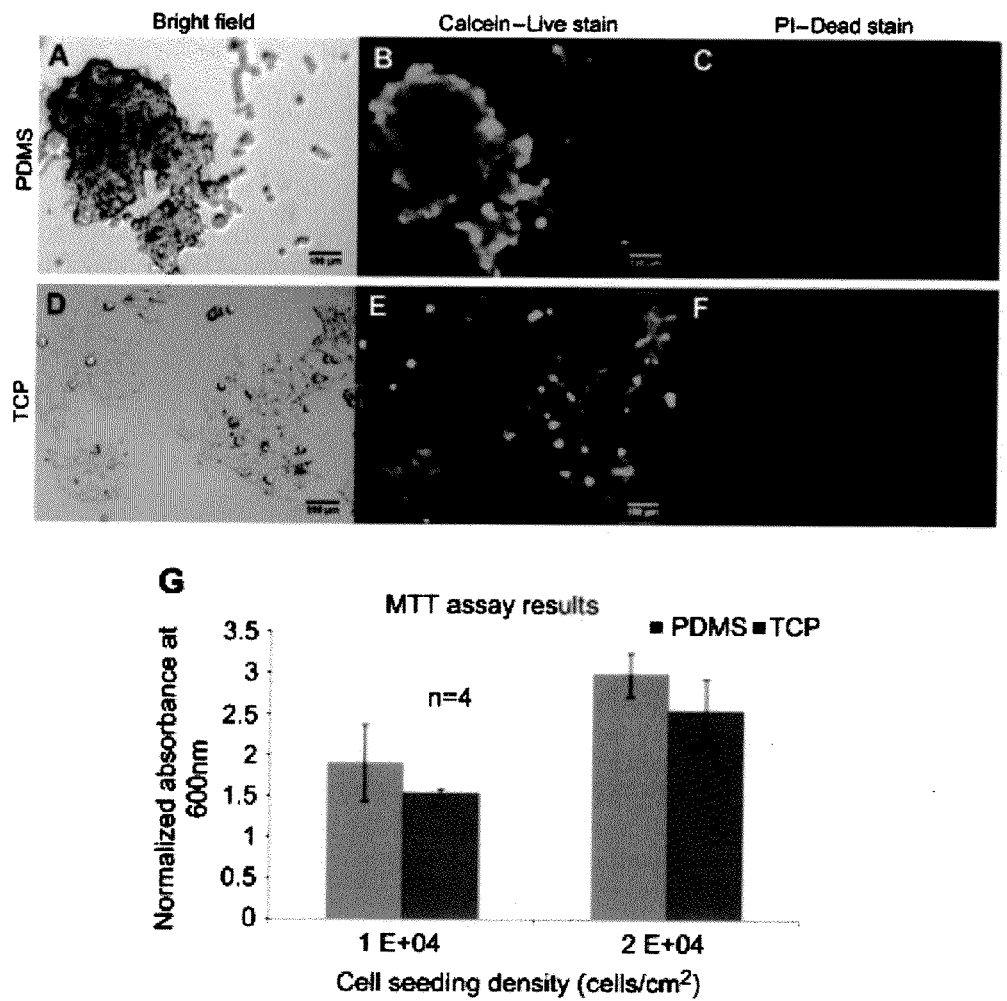
FIGS. 4A-G

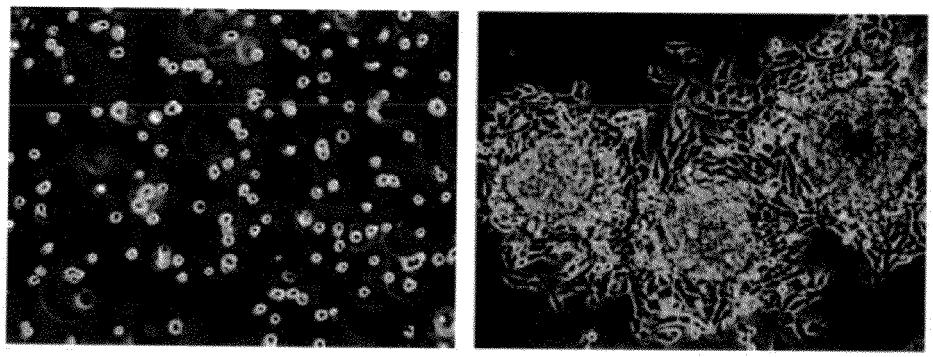
FIGS. 5A-B
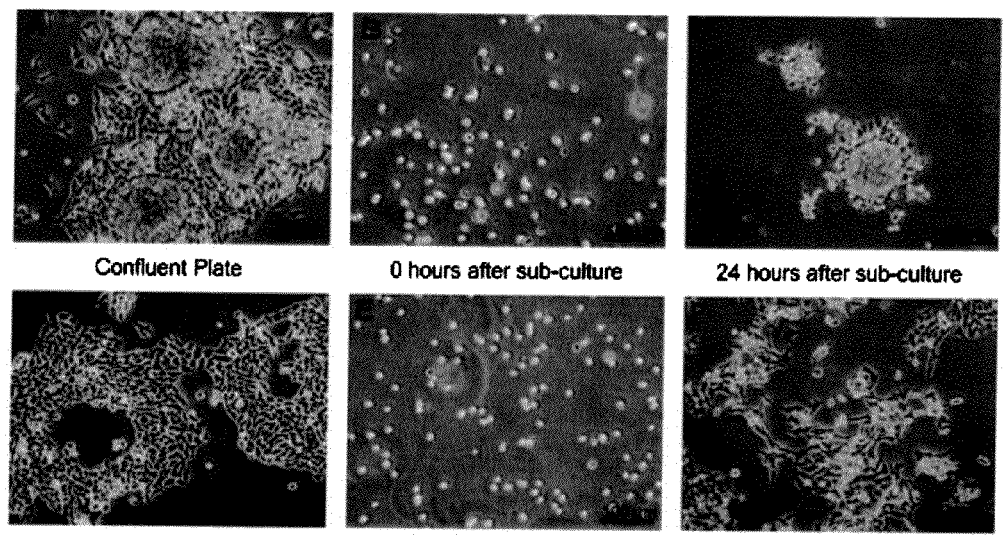
FIGS. 6A-F

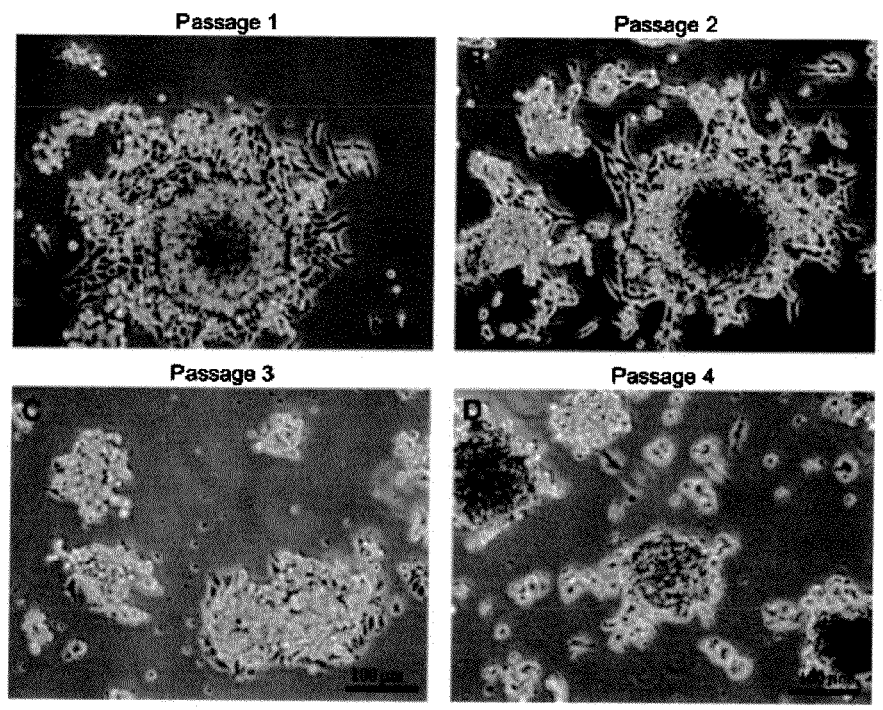
FIGS. 7A-D
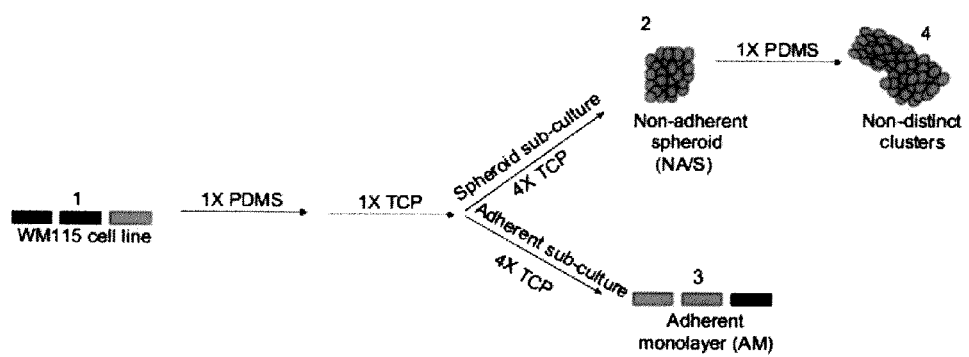
FIG. 8

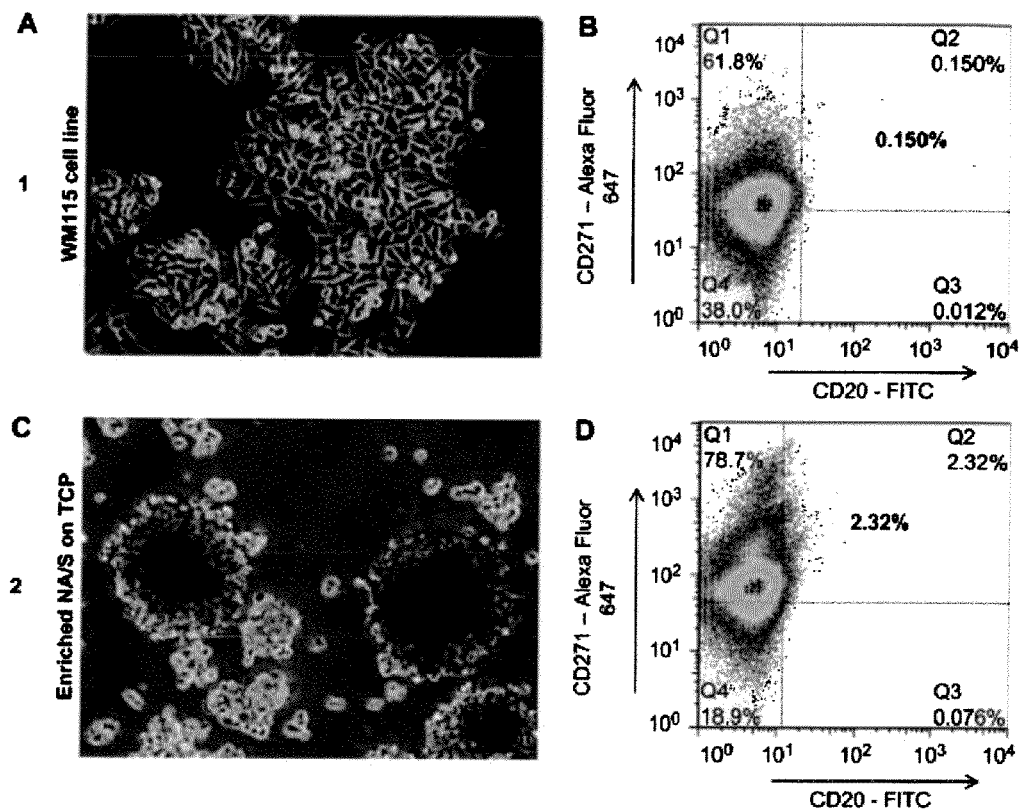
FIGS. 9A-D

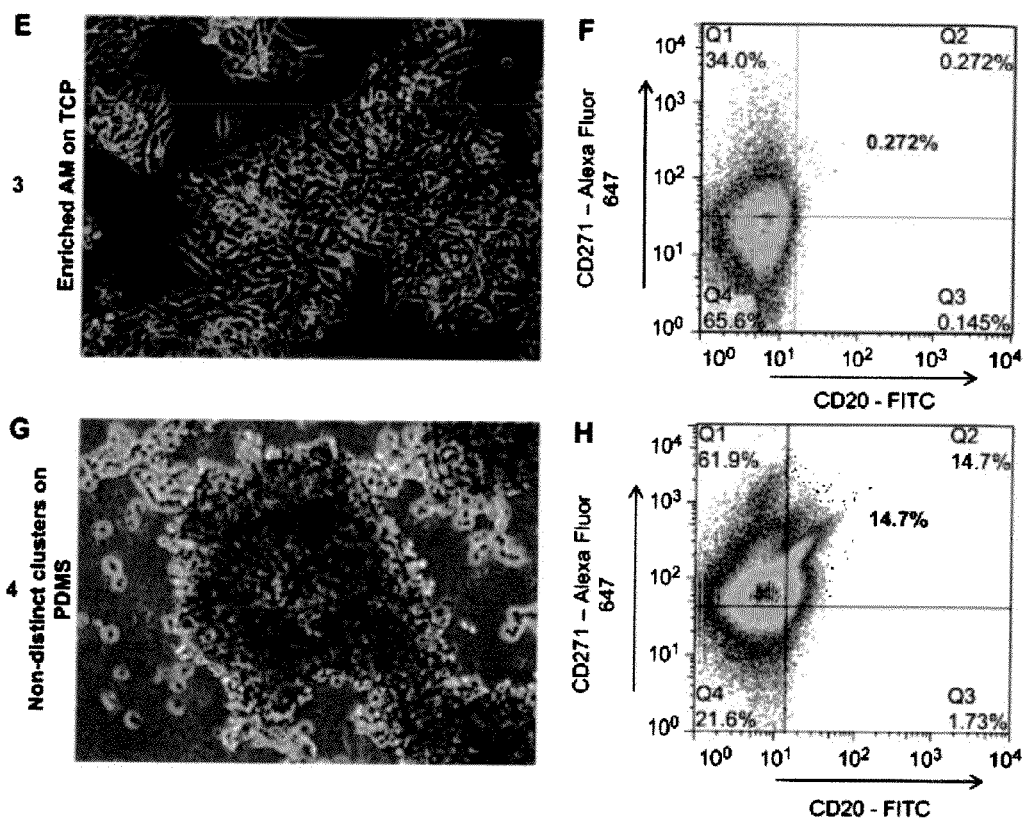
FIGS. 9E-H

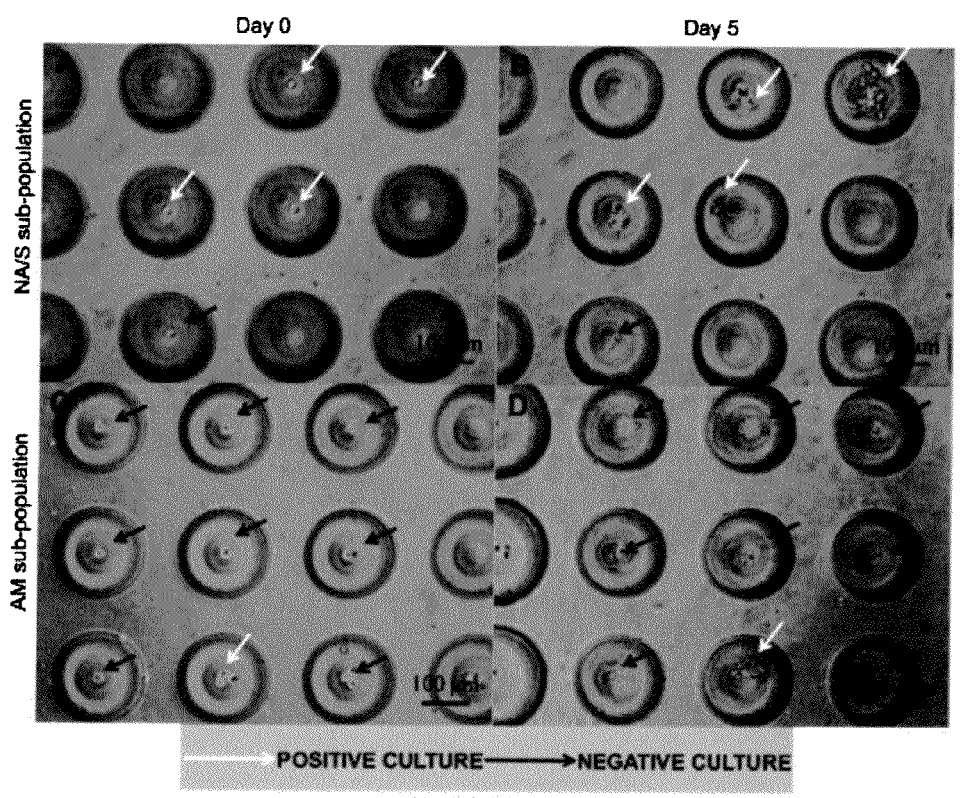
FIGS. 10A-D

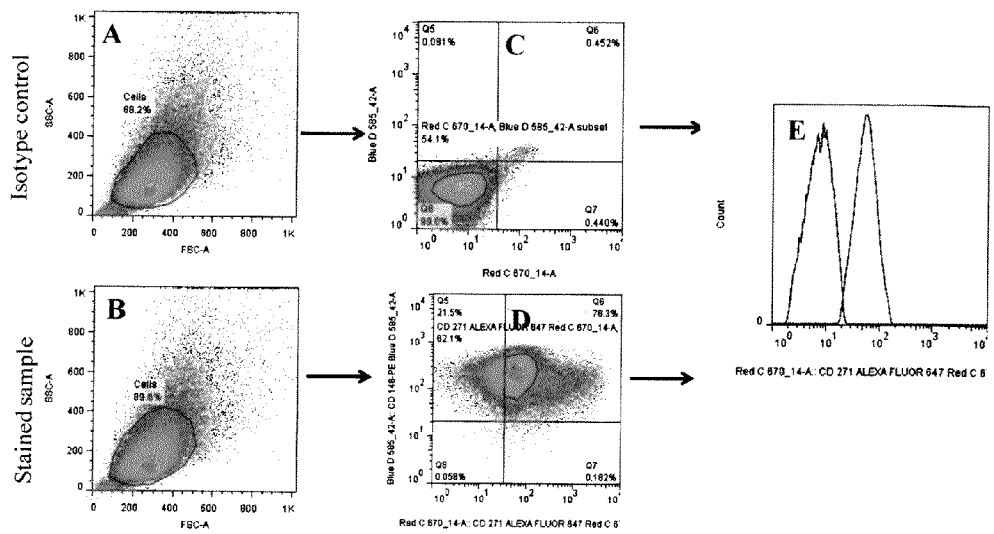
FIGS. 11A-E
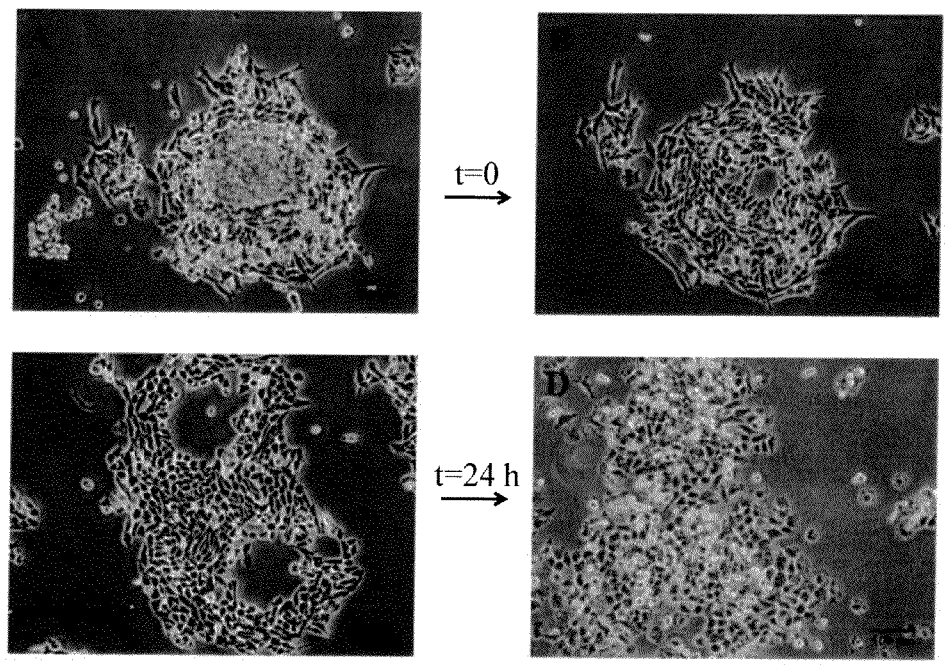
FIGS. 12A-D

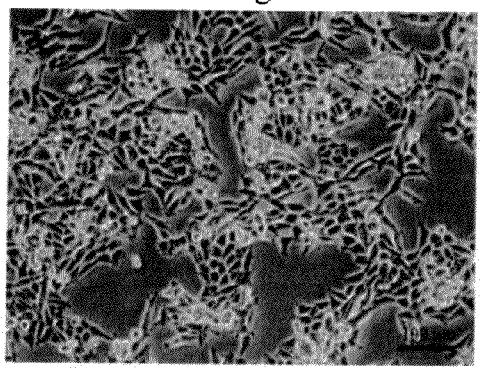 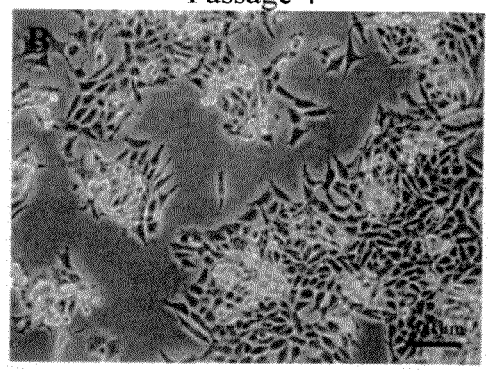
FIGS. 13A-B

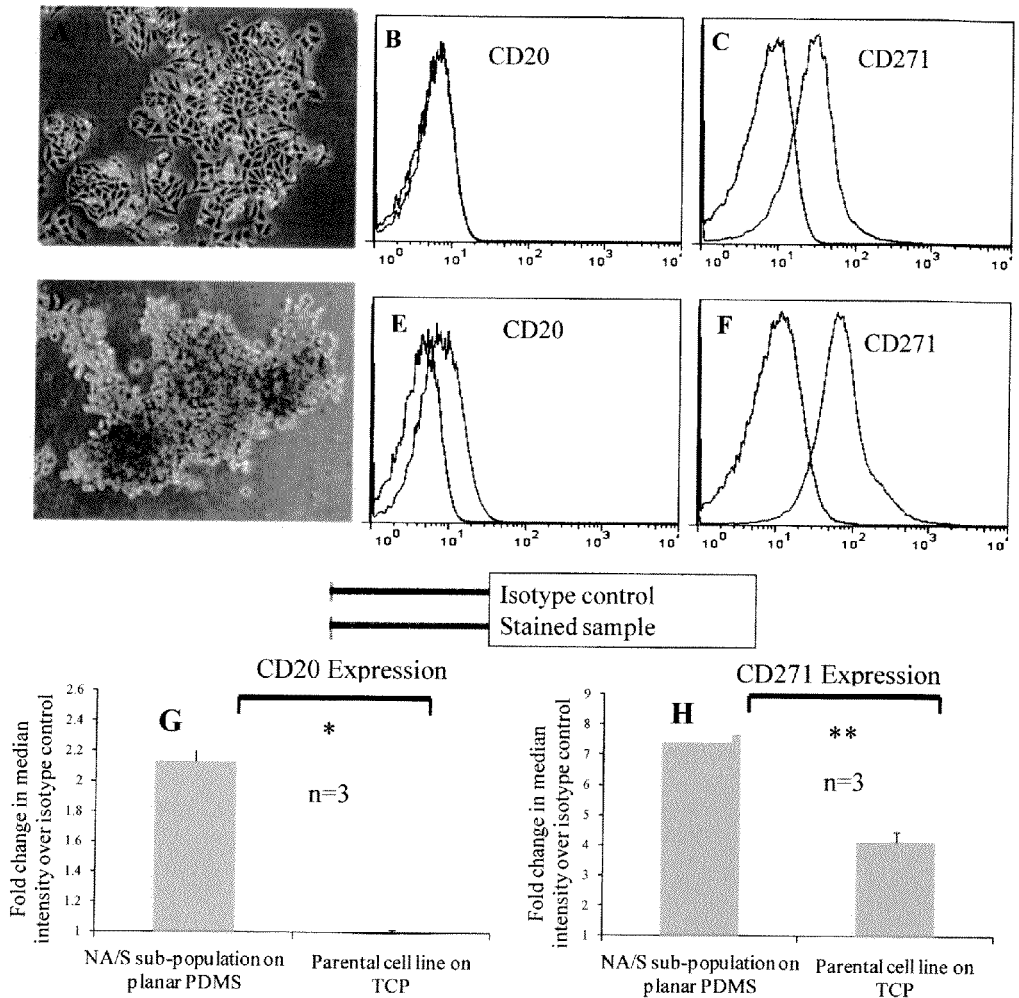
FIGS. 14A-H

METHOD OF ENRICHING STEM AND/OR PROGENITOR CELLS

This invention was made with support from the National Science Foundation under grant CBET 0827862. The U.S. government has certain rights in this invention.

This application claims the priority benefit of U.S. Provisional Patent Application Ser. No. 61/505,881, filed Jul. 8, 2011, which is hereby incorporated by reference in its entirety.

FIELD OF THE INVENTION

This invention relates to novel assays for the enrichment of stem cells (somatic or tumor initiating), and determining the clonogenic potential of such cells. These assays can also be used to sort tumor initiating cells, screen new drugs for their ability to destroy tumor initiating cells or retard their clonogenic potential. The assays are also useful for sorting and characterizing somatic stem or progenitor cells.

BACKGROUND OF THE INVENTION

Somatic (adult) stem cells maintain tissue homeostasis by exhibiting long-term replicative potential, together with the capacities of self-renewal and multi-lineage differentiation. These stem cell properties are tightly regulated in normal development and their alteration can lead to tumorigenesis and metastases (Martínez-Climent et al., "Somatic Stem Cells and the Origin of Cancer," *Clin Transl Oncol.* 8(9):647-63 (2006); Deleyrolle et al., "Determination of Somatic and Cancer Stem Cell Self-renewing Symmetric Division Rate Using Sphere Assays," *PLoS One* 6(1):e15844 (2011)).

Cancer metastases occurs when cells leave the primary tumor, enter circulation, extravasate to a secondary site to initiate a new tumor (Fidler, "The Pathogenesis of Cancer Metastasis: The 'Seed and Soil' Hypothesis Revisited," *Nat Rev Cancer* 3(6):453e8 (2003)). It is estimated that approximately one million cells are shed per gram of a tumor every day (Chang et al., "Mosaic Blood Vessels in Tumors: Frequency of Cancer Cells in Contact with Flowing Blood," *Proc Natl Acad Sci USA* 97(26):14608e13 (2000)). However, only a few of these shed cells have the ability to metastasize (Zhou et al., "Tumour Initiating Cells: Challenges and Opportunities for Anticancer Drug Discovery," *Nat Rev Drug Discov* 8(10): 806e23 (2009); Held et al., "Characterization of Melanoma Cells Capable of Propagating Tumors from a Single Cell," *Cancer Res* 70(1):388e97 (2010)). For a self-reliant circulating tumor cell to successfully metastasize it must possess the ability to interact with and condition the local microenvironment (Ireland et al., "Genetic Factors in Metastatic Progression of Cutaneous Melanoma: The Future Role of Circulating Melanoma Cells in Prognosis and Management," *Clin Exp Metastasis* 28(4):327e36 (2011)). This cell must also have the ability to self-renew and differentiate to drive continuous heterogeneous tumor growth. Cell sub-populations within the primary tumor that have the ability to self-renew, differentiate, and show increased in vivo tumorigenicity are called cancer stem cells (CSCs) (Schatton and Frank, "Cancer Stem Cells and Human Malignant Melanoma," *Pigment Cell Melanoma Res* 21(1):39e55 (2008)). Identifying CSCs and characterizing their cellular origin, phenotype and the mechanisms that confer their tumor-initiating properties have important ramifications for understanding cancer biology and, ultimately, developing cancer cures.

Melanomas are invasive, heterogeneous tumors that are highly resistant to conventional therapies (Schatton and Frank, "Cancer Stem Cells and Human Malignant Melanoma," *Pigment Cell Melanoma Res* 21(1):39e55 (2008); Fang et al., "A Tumorigenic Subpopulation with Stem Cell Properties in Melanomas," *Cancer Res* 65(20):9328e37 (2005); Schatton et al., "Identification of Cells Initiating Human Melanomas," *Nature* 451(7176):345e9 (2008); Boiko et al., "Human Melanoma-initiating Cells Express Neural Crest Nerve Growth Factor Receptor CD271," *Nature* 466 (7302):133e7 (2010); Schmidt et al., "Eradication of Melanomas by Targeted Elimination of a Minor Subset of Tumor Cells," *Proc Natl Acad Sci USA* 108(6):2474e9 (2011); Yang and Chapman, "The History and Future of Chemotherapy for Melanoma," *Hematol Oncol Clin North Am* 23(3):583e97 (2009)). The ability of melanoma to relapse after treatment suggests a lack of knowledge about the biological properties and phenotypes of constituent cell sub-populations and the ineffectiveness of current therapies to eradicate the tumor-initiating cells (DiFronzo et al., "Increased Incidence of Second Primary Melanoma in Patients with a Previous Cutaneous Melanoma," *Ann Surg Oncol* 6(7):705e11 (1999); Cummins et al., "Cutaneous Malignant Melanoma," *Mayo Clin Proc* 81(4):500e7 (2006)). Studies have correlated the tendency of melanoma cells to propagate in vitro as non-adherent spheroids with increased tumor cell invasiveness (Fang et al., "A Tumorigenic Subpopulation with Stem Cell Properties in Melanomas," *Cancer Res* 65(20):9328e37 (2005); Bates et al., "Spheroids and Cell Survival," *Crit. Rev Oncol Hematol* 36(2e3):61e74 (2000); Sodek et al., "Compact Spheroid Formation by Ovarian Cancer Cells Is Associated with Contractile Behavior and an Invasive Phenotype," *Int J Cancer* 124(9):2060e70 (2009); Monzani et al., "Melanoma Contains CD133 and ABCG2 Positive Cells with Enhanced Tumourigenic Potential," *Eur J Cancer* 43(5):935e46 (2007)), and resistance to chemotherapeutics (Bates et al., "Spheroids and Cell Survival," *Crit. Rev Oncol Hematol* 36(2e3):61e74 (2000); Mueller-Klieser, "Three-dimensional Cell Cultures: From Molecular Mechanisms to Clinical Applications," *Am J Physiol* 273(4 Pt 1):C1109e23 (1997); Minchinton and Tannock, "Drug Penetration in Solid Tumours," *Nat Rev Cancer* 6(8):583e92 (2006)). This has lead to the increasing use of the in vitro sphere assay to study melanoma and other types of CSCs (Pastrana et al., "Eyes Wide Open: A Critical Review of Sphere-Formation as an Assay for Stem Cells," *Cell Stem Cell* 8(5):486-98 (2011); Held et al., "Characterization of Melanoma Cells Capable of Propagating Tumors from a Single Cell," *Cancer Res* 70(1): 388e97 (2010); Fang et al., "A Tumorigenic Subpopulation with Stem Cell Properties in Melanomas," *Cancer Res* 65(20):9328e37 (2005); Minchinton and Tannock, "Drug Penetration in Solid Tumours," *Nat Rev Cancer* 6(8):583e92 (2006); Perego et al., "Spheres of Influence in Cancer Stem Cell Biology," *J Invest Dermatol* 131(2):546e7 (2011)). The first evidence that the spheroid cell culture could enrich for CSCs in melanoma came in 2005, when cells propagating as melanospheres exhibited the capacity to undergo multi-lineage differentiation and they exhibited a 10-fold increase in tumorigenicity (ability to form tumors in mice) when compared to cells propagating as a monolayer (Fang et al., "A Tumorigenic Subpopulation with Stem Cell Properties in Melanomas," *Cancer Res* 65(20):9328e37 (2005)). Ramgolam et al. (Ramgolam et al., "Melanoma Spheroids Grown under Neural Crest Cell Conditions Are Highly Plastic Migratory/invasive Tumor Cells Endowed with Immunomodulator Function," *PLoS ONE* 6(4):e18784 (2011)) positively correlated melanoma cells growing as spheroids with a more aggressive phenotype; exhibiting enhanced migratory/invasive characteristics, immune evasion capacity, and ability to differentiate along mesenchymal lineages. They did not, however, observe enhanced self-renewal or tumor initiating capacity in xenotransplantation experiments. Perego et al. (Perego et al., "Spheres of Influence in Cancer Stem Cell Biology," *J Invest Dermatol* 131(2):546e7 (2011); Perego et al., "Heterogeneous Phenotype of Human Melanoma Cells with in vitro and in vivo Features of Tumor-initiating Cells," *J Invest Dermatol* 130(7):1877e86 (2010)) reported xenotransplantion of melanosphere cells into immunocomprised mice resulted in larger tumors compared to recipients of adherent melanoma cells; however, no significant difference in tumorigenicity was observed. The functional ambiguity of cells propagating as melanospheres and the inability to associate a unique set of stem cell surface markers with tumor initiating capacity (Quintana et al., "Efficient Tumour Formation by Single Human Melanoma Cells," *Nature* 456 (7222):593e8 (2008); Quintana et al., "Phenotypic Heterogeneity Among Tumorigenic Melanoma Cells from Patients that Is Reversible and not Hierarchically Organized," *Cancer Cell* 18:510e23 (2010)) has led some to challenge the usefulness of the melanosphere cell culture (Schatton and Frank, "The in vitro Spheroid Melanoma Cell Culture Assay: Cues on Tumor Initiation?" *J Invest Dermatol* 130(7):1769e71 (2010)). It is plausible, however, that these discrepancies may reflect differences in the various methods used to propagate melanospheres and limitations with the methods used to characterize the constituent cell sub-populations (Kubick and Roop, "A Fitness Model for Melanoma-initiating Cells," *Pigment Cell Melanoma Res* 24:396e400 (2011)).

Common approaches used to propagate spheroids include culturing cells in highly mitogenic stem cell media (Fang et al., "A Tumorigenic Subpopulation with Stem Cell Properties in Melanomas," *Cancer Res* 65(20):9328e37 (2005); Ramgolam et al., "Melanoma Spheroids Grown under Neural Crest Cell Conditions Are Highly Plastic Migratory/invasive Tumor Cells Endowed with Immunomodulator Function," *PLoS ONE* 6(4):e18784 (2011)), on soft agar (Hamburger and Salmon, "Primary Bioassay of Human Tumor Stem Cells," *Science* 197(4302):461e3 (1977)), or on Matrigel (Monzani et al., "Melanoma Contains CD133 and ABCG2 Positive Cells with Enhanced Tumourigenic Potential," *Eur J Cancer* 43(5):935e46 (2007); Schatton and Frank, "The in vitro Spheroid Melanoma Cell Culture Assay: Cues on Tumor Initiation?" *J Invest Dermatol* 130(7):1769e71 (2010); Yeung et al., "Cancer Stem Cells from Colorectal Cancer-derived Cell Lines," *Proc Natl Acad Sci USA* 107(8):3722e7 (2010); Civenni et al., "Human CD271-positive Melanoma Stem Cells Associated with Metastasis Establish Tumor Heterogeneity and Long-term Growth," *Cancer Res* 71(8):3098e109 (2011)). These methods are complex, and expensive as growth is usually done under limiting dilution conditions where cells are plating at low density (≤1 cell per well). This is a time consuming process (3-4 weeks), that often requires special media that must be developed through tedious trial-and-error processes. Cells are often prospectively sorted by expression of stem cell markers using flow cytometry, which is an invasive process that can alter cell function and/or viability. In vivo tumorigenicity is characterized using cumbersome and time consuming (1-3 months) animal models that vary in permissiveness; often using serial dilution to quantify the frequency or percent of tumor initiating cells within the heterogeneous cell sample (Fang et al., "A Tumorigenic Subpopulation with Stem Cell Properties in Melanomas," *Cancer Res* 65(20):9328e37 (2005); Schatton et al., "Identification of Cells Initiating Human Melanomas," *Nature* 451(7176):345e9 (2008); Monzani et al., "Melanoma Contains CD133 and ABCG2 Positive Cells with Enhanced Tumourigenic Potential," *Eur J Cancer* 43(5):935e46 (2007); Quintana et al., "Efficient Tumour Formation by Single Human Melanoma Cells," *Nature* 456(7222):593e8 (2008); Quintana et al., "Phenotypic Heterogeneity Among Tumorigenic Melanoma Cells from Patients that Is Reversible and not Hierarchically Organized," *Cancer Cell* 18:510e23 (2010); Welte et al., "Cancer Stem Cells in Solid Tumors: Elusive or Illusive?" *Cell Commun Signal* 8(1):6 (2010)). In vitro clonogenic potential may be determined using limiting dilution cell culture to quantify the frequency of single cells that grow into clonal pure spheres of ~50 cells (Singh et al., "Identification of a Cancer Stem Cell in Human Brain Tumors," *Cancer Res* 63(18):5821e8 (2003)). Given the above mentioned experimental limitations, there is an unmet need for rapid, cost effective nonanimal methods to enrich CSCs from heterogeneous cell sample and to determine the clonogenic potential of constituent cells in a manner that can predict tumorigenic potential.

The present invention is directed to overcoming these and other deficiencies in the art.

SUMMARY OF THE INVENTION

A first aspect of the present invention relates to a method of enriching stem or progenitor cells. This method includes growing a heterogeneous cell sample comprising stem and/or progenitor cells on a first substrate that is hydrophobic and has an elastic modulus less than about 100 MPa; recovering the heterogeneous cell sample from the first substrate; growing the recovered heterogeneous cell sample on a second substrate that is hydrophilic and has an elastic modulus higher than the elastic modulus of the first substrate to produce a subpopulation of nonadherent cells and a subpopulation of adherent cells; and recovering the nonadherent cell subpopulation, which is enriched for stem and/or progenitor cells.

A second aspect of the present invention relates to a method of determining the clonogenic potential of a cell. This method includes providing a microbubble array formed using a substrate that is hydrophobic and has an elastic modulus less than about 100 MPa; seeding one or more microbubbles of the array with one or more cells; growing the cells in the seeded microbubbles; assessing cell proliferation in each seeded microbubble and determining the clonogenic potential of the one or more cells based on said assessed cell proliferation.

A third aspect of the present invention relates to a method of screening an agent for its ability to disrupt cell survival, cell replication, and/or cell differentiation by using a method according to the second aspect of the invention in combination with the introduction of one or more agents to a seeded microbubble and determining whether the introduced one or more agents disrupts cell survival, cell replication, and/or cell differentiation.

The accompanying Examples demonstrate, in one embodiment, a simple in vitro method using inexpensive polydimethylsiloxane (PDMS) as a cell culture substrate for enriching non-adherent spheroid (NA/S) and adherent monolayer (AM) sub-populations from a metastatic melanoma and breast cancer cell lines. This method leverages a hydrophobic substrate to encourage cell-cell contacts but, importantly, does not require use of special stem cell media. The phenotypes of the enriched melanoma sub-populations were investigated by studying the expression of stem-cell markers CD20 (a B-lymphocyte antigen) and CD271 (neural crest stem-cell marker) using flow cytometry.

The accompanying Examples also demonstrate, in one embodiment, the use of PDMS microbubble arrays to determine the clonogenic potential of these enriched NA/S and AM sub-populations. Microbubbles are spherical cavities formed in PDMS using the gas expansion molding (GEM) process (Giang et al., "Microfabrication of Cavities in Polydimethylsiloxane using DRIE Silicon Molds," *Lab Chip* 7(12):1660e2 (2007), which is hereby incorporated by reference in its entirety). The microbubble cell culture platform is ideally suited for studying CSCs in the tumor microenvironmental niche, which is composed of soluble factors, extracellular matrix (ECM) proteins, cell-cell contacts and mechanical loading. These factors determine the clonogenic and tumorigenic potential in vivo and govern whether a cell can self-renew and/or differentiate into a tumor or normal cell or remain quiescent (Bissell et al., "Context, Tissue Plasticity, and Cancer: Are Tumor Stem Cells also Regulated by the Microenvironment?" *Cancer Cell* 7(1):17e23 (2005); Ghotra et al., "The Cancer Stem Cell Microenvironment and Anticancer Therapy," *Int J Radiat Biol* 85(11):955e62 (2009), each of which is hereby incorporated by reference in its entirety). The advantage of using microbubbles for culturing enriched cell sub-populations derives from the fact that all the properties of the cell microenvironment can be specifically investigated; the geometry allows for the accumulation of autocrine/paracrine factors while permitting sufficient nutrient and waste exchange with the bulk media reservoir through the microbubble opening (Chandrasekaran et al., "Microenvironment Induced Spheroid to Sheeting Transition of Immortalized Human Keratinocytes (HaCaT) Cultured in Microbubbles Formed in Polydimethylsiloxane," *Biomaterials* 32(29):7159e68 (2011), which is hereby incorporated by reference in its entirety). The surface of microbubble can be coated with proteins of interest (Giang et al., "Microfabrication of Bubbular Cavities in PDMS for Cell Sorting and Microcell Culture Applications," *J Bionic Eng* 5(4):308e16 (2008), which is hereby incorporated by reference in its entirety), there is room for cell-cell contacts inside the microbubble and the elastic modulus of PDMS closely resembles in vivo tissue thereby providing a more realistic mechanical load (Janmey and Miller, "Mechanisms of Mechanical Signaling in Development and Disease," *J Cell Sci* 124(Pt 1):9e18 (2011), which is hereby incorporated by reference in its entirety). The microbubble cell culture platform enables rapid (~5-7 days) generation of pure clones from single cells and eliminates concerns for clone aggregation that may occur when cells are plated at high clonal densities to enable their survival in standard limiting dilution assay conditions (Pastrana et al., "Eyes Wide Open: A Critical Review of Sphere-formation as an Assay for Stem Cells," *Cell Stem Cell* 8(5):486e98 (2011); Fedoroff and Richardson, "Colony Cultures—Plating Efficiency Assay and Cloning, in Protocols for Neural Cell Culture," 307e315, Humana Press, doi:10.1385/1-59259-207-4 (2001), each of which is hereby incorporated by reference in its entirety).

BRIEF DESCRIPTION OF THE DRAWINGS

FIG. 2 is a schematic illustration of a microfluidic device that includes an integrated microbubble array.

FIG. 3A-B are images illustrating the morphology of the WM115 tumorigenic melanoma cell line grown on TCP (3A) and planar PDMS (3B). WM115 cell line was propagated for 3 days as an adherent monolayer on TCP and as nonadherent 3D clusters on planar PDMS, respectively. Initial seeding density=$2\times10^4$ cells/cm$^2$. Scale bars=100 mm.

FIGS. 4A-G illustrate the results of cell viability assays for WM115 cell line on planar PDMS (4A-C) and TCP (4D-F). Calcein-AM/Propidium iodide (PI) assay for live cells (4B, 4E) and dead cells (4C, 4F), respectively, indicate that cells are viable on both planar PDMS (4B) and TCP (4E) with few dead cells on planar PDMS (4C) and TCP (4F). MTT assay for metabolic activity indicate that there is no statistically significant difference (p>0.1) in the metabolic activity of cells on planar PDMS and TCP (4G).

FIGS. 5A-B are images illustrating the sub-culturing of WM115 cell line from planar PDMS to TCP. WM115 cell line from planar PDMS dissociated and plated as single cells on hydrophilic TCP (5A). By the end of day 4, cells emerge with two distinct morphologies comprised of spheroid forming cells surrounded by an adherent layer (5B). Initial seeding density=$1\times10^4$ cells/cm$^2$. Scale bars=100 mm.

FIGS. 6A-F illustrate the sub-culturing nonadherent/sphere forming (NA/S) and adherent monolayer (AM) sub-populations derived from the heterogeneous WM115 cell line. The NA/S cells were removed by pipetting the media from a confluent plate (6A) and were dissociated and plated as single cells on a fresh TCP (6B). After 24 h, the NA/S cells formed NA/S again (6C). After removing the spheroids the AM cells (6D) were trypsinized and plated as single cells on a fresh TCP (6E). After 24 h sub-culture they reformed AM cells only (6F). Initial seeding density=$1\times10^4$ cells/cm$^2$. Scale bars=100 mm.

FIGS. 7A-D illustrate that passaging the NA/S sub-population of WM115 on TCP resulted in the reduction of adherent cells. Sub-culturing spheroid cells resulted in cells showing "fried egg" morphology by the end of day 4 (7A). By passaging spheroid cells successively on TCP, the fraction of adherent cells diminished progressively (7B-D) and by the end of passage 4, there was a very small fraction of cells forming adherent cells (7D). All images were taken on day 4 after sub-culture. Initial single cell seeding density=$1\times10^4$ cells/cm$^2$. Scale bars=100 mm.

FIG. 8 is a schematic illustration of an assay protocol used to enrich cells with CSC phenotype in WM115 cell line. The numbers indicate the points at which the cells were probed for the expression of CD20 and CD271.

FIGS. 9A-H illustrate the morphology and surface marker phenotypes of cell samples derived from the WM115 cell line at different stages during the assay. Only 0.15% of the WM115 cell line propagated as a monolayer on TCP (9A) is CD20+ and CD271+ (9B). The assay generated two sub-populations of cells capable of propagating as NA/S on TCP (9C) and AM on TCP (9E) with different phenotype as depicted by the scatter plots (9D and 9F). When the enriched NA/S sub-population was dissociated and seeded back onto planar PDMS they adopted non-distinct 3D cluster morphology (9G) with 14.7% of the cells being CD20+ CD271+ (9H).

FIGS. 10A-D are selected images illustrating the fate of some of the cells from the NA/S and AM sub-populations in microbubble colongenic potential assay. Microbubble arrays (>1600 MB wells) were imaged immediately after seeding with cells from the NA/S sub-population (10A) and AM sub-population (10C). The same locations in the arrays were imaged after 5 days in culture (10B and 10D). Positive cultures are denoted by white arrows and negative cultures are denoted by black arrows.

FIGS. 11A-E illustrate one representative example of the gating process used to analyze the CSC phenotypes derived from the WM115 cell line. Scatter plot between FSC and SSC for isotype control (11A) and stained sample (11B) gated for cell population based on the relative size and granularity. The fluorescent scatter plots with all the cells in isotype control confined to the lower left quadrant (11C) and the corresponding plot with quad-gate for stained sample (11D). The histogram in FIG. 11E shows the relative shift in fluorescent intensity of stained sample (right peak) with respect to isotype control (left peak).

FIGS. 12A-D illustrate the effects of incubating the AM sub-population with cell culture media after the removal of spheroid sub-population. The WM115 cell line sub-cultured from planar PDMS to TCP before (12A) and after (12B) the removal of the NA/S sub-population. Incubating the AM cells after removing the spheroids (12C) with media for 24 hours results indicate that the AM cells were not capable of producing NA/S sub-population (12D).

FIGS. 13A-B illustrate the effect of passaging the AM sub-population on TCP. When the AM sub-population from the "fried egg" morphology was sub-cultured on TCP it resulted in cells propagating as a monolayer (13A). Subsequently passaging them on TCP resulted in the enrichment of cells that retained the ability to propagate as a monolayer, which is evident from their morphology by the end of passage 4 (13B).

FIGS. 14A-H illustrate the changes in the expression levels of CD20 and CD271. WM115 cell line propagating as a monolayer on TCP (14A) do not express CD20 (14B) and there is a base level expression of CD271 (14C). The enriched NA/S sub-population that was seeded on planar PDMS (14D) exhibit a stronger expression of both CD20 (14E) and CD271 (14F) when compared to cells propagating as a monolayer on TCP. The bar graphs indicate that there is a significant change in expression of CD20 ($p<0.05$) (14G) and CD271 ($p<0.01$) (14H).

DETAILED DESCRIPTION OF THE INVENTION

Figure 1:
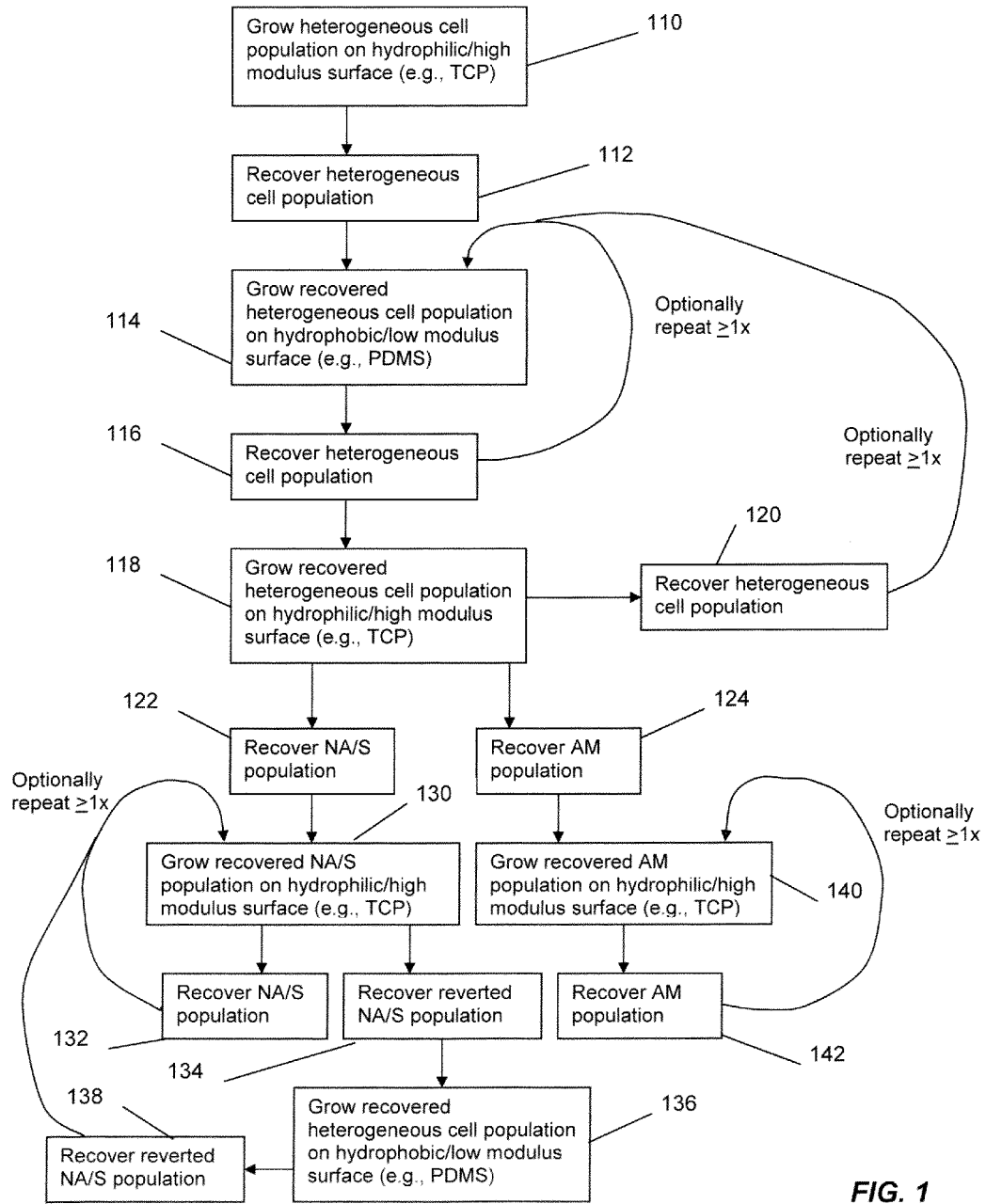
FIG. 1 illustrates a process for the enrichment of stem and/or progenitor cells from heterogeneous cell populations.

The present invention relates to novel in vitro assays for the enrichment of stem and/or progenitor cells from heterogeneous cell populations, as well as in vitro assays for assessing the clonogenic potential of various cell sub-populations, including somatic stem or progenitor cells and cancer stem cell sub-populations enriched using the enrichment assay described herein. As described herein, both of these assays can also be used as platforms to assess the ability of an agent to disrupt cell survival, cell replication, and/or cell differentiation, particularly the survival, replication, and/or differentiation of certain stem or progenitor cell sub-populations.

As used herein, the term "somatic stem cell" is used generically to refer to a type of cell within a tissue that possesses a capacity to self-renew and differentiate, but such capacity is usually (though not necessarily) limited to the types of differentiated cells present in the tissue of origin. In contrast, the term "somatic progenitor cell" refers to a cell that possesses a limited capacity to self-renew and is much more limited in the types of differentiated cells that it can become.

As used herein, the terms "cancer stem cell" (or CSC) and "tumor-initiating cell" and "cancer-initiating cell" are used interchangeably to refer to a type of cell within a tumor that possesses the capacity to self-renew and to cause the heterogeneous lineages of cancer cells that comprise the tumor. Thus, these CSCs are but one type of cell sub-population that may exist within a tumor. This definition does not indicate the source of these CSCs, because these tumor-forming cells may originate from stem, progenitor, or differentiated cells.

As used herein, the term "sub-population" refers to a subset (or fraction) of a larger population, where the subset shares a particular phenotype or characteristic. With respect to cell subpopulations, different subpopulations will have at least one phenotypic difference that distinguishes it from another subpopulation. Such phenotypic differences can be measured by cell behavior in different cell culture environments, different levels of gene expression or protein expression (e.g., a particular cell surface marker or nuclear marker), morphology, migratory behavior, invasiveness (e.g., Matrigel assay), etc. A cell sample obtained following the enrichment assay described herein can be enriched for a particular subpopulation (i.e., comprising a higher percentage than before), or be an essentially pure sample that consists of only the cells from a particular subpopulation.

One aspect of the present invention relates to a method of enriching stem or progenitor cells. This method includes growing a heterogeneous cell sample that contains one or more stem and/or progenitor cells on a first substrate that is hydrophobic and has an elastic modulus less than about 100 MPa; recovering the heterogeneous cells from the first substrate; growing the recovered heterogeneous cells on a second hydrophilic substrate having an elastic modulus higher than the elastic modulus of the first substrate to produce a subpopulation of nonadherent cells and a subpopulation of adherent cells; and recovering the nonadherent cell subpopulation (i.e., from the second substrate), which is enriched for stem or progenitor cells (or both).

The initial heterogeneous cell sample can be from a cell line or a sample derived from a patient. For patient-derived samples, the samples can be obtained from any type of tissue. In certain embodiments, the cell sample is a cancer cell sample, i.e., obtained from one or more tumor biopsies.

In certain embodiments, the steps of growing the recovered heterogeneous cells on the second substrate and recovering the nonadherent cell subpopulation can be repeated for two or more rounds, three or more rounds, four or more rounds, or even five to ten more rounds, or more than ten rounds. In addition, recovered nonadherent cells can be subcultured on the first substrate to further enrich this phenotype; use of the first and second substrates may therefore be alternating or multiple successive rounds on one substrate followed by multiple successive rounds on the other substrate. Each successive round should result in further enrichment and possibly transformation of the nonadherent cells, although diminishing degrees of enrichment/transformation will occur after a certain number of rounds. As a consequence of passaging the cell subpopulations in this manner, the enriched/transformed subpopulation of nonadherent cells are phenotypically distinct from the subpopulation of adherent cells.

In certain embodiments, alternating additional steps of growing the recovered heterogeneous cells on the first substrate, followed by their recovery, growing the recovered cells on the second substrate, and finally recovering the nonadherent cell subpopulation can be repeated for two or more rounds, three or more rounds, four or more rounds, or even five to ten more rounds, or more than ten rounds In this first aspect of the invention, the first substrate is hydrophobic and has an elastic modulus less than about 100 MPa. In certain embodiments, the elastic modulus of the first substrate is between about 100 Pa to about 50 MPa, more preferably about 1 kPa to about 30 MPa, or about 10 kPa to about 10 MPa. In certain embodiments, the hydrophobic substrate has a surface energy of less than about 30 dynes/cm, more preferably less than about 20 dynes/cm; exhibits an air-water contact angle that is greater than about 80 degrees, preferably greater than about 90 degrees or even greater about 100 degrees; or both.

Examples of suitable hydrophobic substrates include, without limitation, natural rubbers, butyl rubbers, silicone rubbers, urethane rubbers, acrylic rubbers, polysulfide rubbers, butadiene rubbers, neoprene rubbers, isoprene rubbers, silicones, polydimethylsiloxane (PDMS), low density poly(ethylene-covinyl acetate), low density polyethylene, low density polyurethane, fluorinated versions of the aforementioned substrates, and copolymers thereof. As is well known in the art, these substrates can be surface modified to include biological reagents tethered to their surface.

Natural and modified rubbers typically have an elastic modulus of between about 1 to about 5 MPa, although urethane rubbers typically have a slightly higher elastic modulus of about 2 to about 10 MPa whereas neoprene rubbers typically have a slightly lower an elastic modulus of about 0.7 to about 2 MPa.

Silicones typically have an elastic modulus of about 5 to about 20 MPa.

PDMS can be fabricated with varying conditions in the ratio of the base and cross linker components, or by using different curing conditions (temperature and duration) or post-treatment oxidation to achieve PDMS substrates having elastic moduli ranging from about 0.4 kPa to about 300 kPa (Gutierrez and Groisman, "Measurements of Elastic Moduli of Silicone Gel Substrates with a Microfluidic Device," *PLoS One* 6(9): e25534 (2011); Lee et al., "Compatibility of Mammalian Cells on Surfaces of Poly(dimethylsiloxane)," *Langmuir* 20:11684-11691 (2004), each of which is hereby incorporated by reference in its entirety.

Low density polyurethanes can be fabricated using known conditions to achieve polymers having an elastic modulus between about 70 MPa to about 100 MPa.

Low and medium density polyethylene can be fabricated using known conditions to achieve polymers having an elastic modulus of between about 38 to about 75 MPa.

Low density poly(ethylene-covinyl acetate) can be fabricated using known conditions to achieve polymers having an elastic modulus between about 48 MPa to about 100 MPa.

In this first aspect of the invention, the second substrate is hydrophilic and has an elastic modulus of at least about 500 MPa. In certain embodiments, the hydrophilic substrate has a surface energy of greater than about 40 dynes/cm, more preferably greater than about 50 or about 60 dynes/cm; exhibits an air-water contact angle that is less than about 50 degrees, preferably less than about 30 degrees, or even less than about 20 or even less than about 10 degrees; or both.

Examples of suitable second substrates include, without limitation, glasses, and plasma-treated polymers (e.g., use of oxygen plasma stabilized in helium at atmospheric pressure to increase the surface energy and improve wetting characteristics, as described in Thurston et al., "Effect of Atmospheric Plasma Treatment On Polymer Surface Energy and Adhesion," *J Plastic Film and Sheeting* 23(1):163-78 (2007), which is hereby incorporated by reference in its entirety)) including polystyrene, polystyrene/acrylonitrile copolymers, high density polyurethanes, high and medium density polyethylenes, polyamides, polypropylenes, and polyvinylchlorides. Of these, glass and plasma-treated polystyrene are most often used for cell culture purposes, and each has a suitably high elastic modulus. As is well known in the art, these substrates can be surface modified to include biological reagents tethered to their surface.

In one embodiment, the first substrate is PDMS and the second substrate is glass. In another embodiment, the first substrate is PDMS and the second substrate is polystyrene.

Regardless of the materials selected for the first and second substrates, the material is preferably fabricated in the form of a multi-well plate that contains multiple wells of essentially the same volume. Multi-well plates of this structure are well known in the art.

In the various embodiments of this method, the cell populations grown on the first substrate and the second substrate can be grown in any suitable cell culture medium. Cell culture media normally needed for stem cell maintenance is not necessarily required. Examples of suitable cell culture media include, without limitation, MEM, DMEM, HMEM, EMEM, Hank's solution, JCI99, OPTIMEM, and RPMI 1600. These media can be supplemented, as desired, with one or more additional additives, including serum, insulin, growth promoters, L-glutamine, buffer, heparin, steroids or steroid-like compounds, chondroitin sulfate, pyruvate, ascorbic acid, ascorbate, a collagen or elastin cross-linking agent, a co-enzyme, pathway inhibitors, signaling proteins or compounds, gene or protein transfection agents, and antibiotic agents. Alternatively, if desired, suitable stem cell media can be utilized.

Growing of the cell populations (on the first and second substrates) can be carried out for any suitable amount of time to allow for differentiation of the populations. Typically this involves growing the cell populations anywhere from about 18 to about 120 hours, preferably 48 to 96 hours. As demonstrated in the Examples, excellent results have been achieved while growing the cell populations for about 72 hours.

In this first aspect of the invention, the recovering the heterogeneous cells from the first substrate and the recovering of the nonadherent cell subpopulation can be achieved by any suitable process for cell recovery. Exemplary approaches for cell recovery from a cell culture depends on whether the cell population to be recovered includes adherent cells, non-adherent or loosely adherent cells, or a mixture thereof. For non-adherent or loosely adherent cells, aspiration by vigorous pipetting, shaking or rocking of a culture vessel, gently scraping, or any other suitable procedures may be utilized. For adherent cells, enzymatic dissociation (e.g., trypsin, cymotrypsin, dispase, hyaluronidase, heparinase, collagenase, with or without calcium chelators EDTA or EGTA, or both) is usually utilized alone or in combination with aspiration.

Ultimately, this process allows for the isolation of a highly enriched population of somatic stem or progenitor cells or cancer stem cells.

Enriched somatic stem or progenitor cells can be studied to identify approaches for manipulating the differentiation processes to treat disease or injury.

Enriched cancer stem cells can be studied and screened to identify effective therapies or combinations of therapies that can reduce the cancer stem cell clonogenic potential. Thus, in one approach, following one or more tumor biopsies, the recovered heterogeneous population can be enriched for cancer stem cells, and then the enriched cancer stem cells screened for their clonogenic potential as well combinations of chemotherapeutic agents that are effective in killing the cancer stem cells or reducing their clonogenic potential.

Several embodiments of this enrichment process are illustrated in FIG. 1. Initially, at step 110, a heterogeneous cell sample is plated onto hydrophilic/high modulus surface (e.g., polystyrene TCP) in suitable media and then grown. At step 112, the heterogeneous cell sample is recovered from the hydrophilic/high modulus surface, and then passaged at step 114 onto hydrophobic/low modulus surface (e.g., PDMS) in suitable media and then grown. At step 116, the heterogeneous cell sample is recovered from the hydrophobic/low modulus surface. Optionally, steps 114 and 116 are repeated one or more times before proceeding to step 118, where the heterogeneous cell sample recovered from the hydrophobic/low modulus surface is then plated at step 120 onto a hydrophilic/high modulus surface (e.g., polystyrene TCP) in suitable media and then grown. In one embodiment, the preceding steps are sufficient to give rise to two distinct populations of cells—nonadherent spheroidal cells (NA/S) and adherent monolayer cells (AM), which can be separately recovered at steps 122 and 124, respectively, using the procedures described above and in the Examples. In an alternative embodiment, a heterogeneous cell sample is recovered at step 120, and steps 114, 116, and 118 are repeated until NA/S and AM populations are recovered at steps 122 and 124. Regardless, once these distinct cell types are obtained, they can be separately handled in subsequent enrichment steps.

At step 130, the NA/S population is plated onto a hydrophilic/high modulus surface (e.g., polystyrene TCP) in suitable media and grown, and then recovered at step 132. This NA/S population can be reprocessed through steps 130 and 132 for multiple passages as long as the NA/S phenotype is maintained.

If during step 130, the enrichment of the NA/S phenotype is lost (e.g., reverted phenotype), then the cells obtained at step 134 can be passaged at step 136 onto hydrophobic/low modulus surface (e.g., PDMS) in suitable media and grown, and then recovered at step 138. The recovered cell population can optionally be repeatedly passaged onto the hydrophilic/high modulus surface (e.g., polystyrene TCP) in suitable media (step 130) until the NA/S population is again recovered.

For the AM population recovered at step 126, these cells can be passaged at step 140 onto the hydrophilic/high modulus surface (e.g., polystyrene TCP) in suitable media and grown, and then recovered at step 142. This process can be repeated as desired.

One particular embodiment of this cell enrichment process is illustrated in FIG. 8 and the accompanying Examples for the recovery of enriched melanoma CSCs.

A further aspect of the present invention relates to a method of determining the clonogenic potential of a cell sample, particularly a sample containing stem cells, more particularly cancer stem cells or somatic stem or progenitor cells. This method includes the steps of providing a microbubble array formed using a substrate that is hydrophobic and has an elastic modulus less than about 100 MPa; seeding the microbubble array with one or more cells; growing the cells in the microbubble array; and assessing cell proliferation in each microbubble, and determining the clonogenic potential of the one or more cells.

The microbubble array can be formed using a substrate that is hydrophobic and has an elastic modulus less than about 100 MPa. Exemplary substrates of this type are described above, with PDMS (e.g., Dow Corning Sylgard® 184) being preferred. Fabrication of the microbubble array can be carried out using the procedures described in Giang et al., "Microfabrication of Bubbular Cavities in PDMS for Cell Sorting and Microcell Culture Applications," *J Bionic Eng* 5(4):308e16 (2008); Giang et al., "Micro fabrication of Cavities in Polydimythylsiloxane Using DRIE Silicon Molds," *Lab on a Chip* 7:1660-1662 (2007); and WO/2008/157480, each of which is hereby incorporated by reference in its entirety. Briefly, PDMS is cast over a silicon wafer mold containing deep etched pits that can vary in opening shape and size, e.g., about 20 to about 200 μm square, triangular, circular or rectangular openings, and surface-treated to render the silicon mold hydrophobic with a water contact angle greater than 100 degrees. The PDMS premix is allowed to settle at room temperature for about 30 minutes to allow air trapped in the PDMS premix to rise to the liquid/air interface and the premix to self-level. Thereafter, the PDMS cast on the wafer mold is incubated at elevated temperature for a suitable duration to cause expansion of the air in the trench and microbubble formation (e.g., about 100° C. for 10 minutes to 2 hours). Incubating at high temperature >65° C. forms a meniscus over the pit and serves to nucleate further bubble growth as air trapped in the PDMS diffuses to the growing bubble. Surface tension at the pit opening overcomes buoyancy preventing detachment of the microbubble. Thus, the rising and expanding air allows for formation of the microbubble array. The etched pattern will dictate the spacing of the microbubbles as well as their shape and volume. Importantly, conventional vacuum degassing is not used and overnight curing of the PDMS at room temperature is not used without a high temperature incubation step, as both of these processes hinder formation of the microbubbles.

In certain embodiments, the microbubble array is formed with microbubbles having a volume of between about 2-10 mL or 2-8 mL, although preferably the microbubbles have a volume of about 4-5 mL. Regardless of their volume, the microbubbles are characterized by a reduced dimension opening formed in the common planar surface of the PDMS substrate.

The interior surface of the microbubbles can be provided with any desired surface chemistry or coatings or biomolecules to affect cell growth, adhesion, or proliferation. It is also possible to coat both the planar surface of the array with a different surface chemistry or coating or biomolecule relative to that provided within the microbubbles. For example, using the vacuum-assisted coating technique described in Giang et al., "Micro fabrication of Bubbular Cavities in PDMS for Cell Sorting and Microcell Culture Applications," *J Bionic Eng* 5(4):308e16 (2008), which is hereby incorporated by reference in its entirety, it is possible to block the planar surface with, e.g., BSA and subsequently coat the microbubble interior surface with a chemotactic biomolecule or extracellular matrix molecule to enhance cell capture or a bioactive molecule to direct cell fate.

As shown in FIG. 2, a microfluidic device 10 includes an integrated microbubble array 12 with a media bulk reservoir 14. Although only four microbubbles 15 are shown in cross-section, it should be appreciated that the array can be fabricated with any number of microbubbles in a planar array (see WO/2008/157480, which is hereby incorporated by reference in its entirety). As shown, the reservoir 14 can be continually or periodically perfused with fresh media, if desired, via an inlet 16 and an outlet 18. By virtue of the structure of the microbubble array, including the size of the openings 20 formed in the planar surface 22 of the PDMS substrate 24, cells growing within each microbubble are removed from any shear stress from the flow of media, while allowing for free exchange of nutrients and waste, as well as any other agents introduced via the media.

It is also possible to culture cells in microbubble arrays in a static mode where the microbubble array chip is placed in a well of a standard tissue culture plate (TCP) and the chip is immersed in a volume of media appropriate for the size of the standard well, e.g. 1 ml in a well of a 24-well tissue culture plate.

In use, the array will be seeded with one or more cells per microbubble, preferably from one to three cells per microbubble, and then the cells can be incubated in appropriate media using, e.g., a microfluidic device of the type illustrated in FIG. 2 or in static culture. Cells are allowed to grow for a suitable duration of time to assess their clonogenic potential, which is typically up to seven days, more typically up to five days, e.g., three to five days. The assay time can be varied to alter the stringency of the clonogenic potential assay. After sufficient growth period, cell proliferation in each microbubble is assessed by scoring each microbubble for cell growth or absence of cell growth, counting the number of cells present in each microbubble, or both. Cell growth can be measured by eye or using appropriate live/dead stains known to those skilled in the art. The result of this assessment can be used to determine the clonogenic potential of the one or more cells used to seed the microbubbles or the cell sample itself. As demonstrated in the accompanying Examples, determining the clonogenic potential of cancer stem cells can be achieved using an Extreme Limiting Dilution Analysis (ELDA). ELDA is a software application for limiting dilution analysis, with particular attention to the needs of stem cell assays (Hu et al., "ELDA: Extreme Limiting Dilution Analysis for Comparing Depleted and Enriched Populations in Stem Cell and Other Assays," *J. Immunol. Method* 347(1-2): 70-8 (2009), which is hereby incorporated by reference in its entirety). The software is available on the Walter and Eliza Hall Institute of Medical Research web site.

Further aspects of the present invention relate to methods of screening an agent (or a combination of agents) for its ability to disrupt cell survival and/or cell replication.

According to one approach, the microbubble array is used to screen the clonogenic potential of a heterogeneous population of cancer cells or enriched cancer stem cell in the presence or absence of the agent or the combination of agents. The agent or agents can be introduced to the cell sample via media containing soluble factors, by exposing the seeded microbubble array to radiation or other forms of energy, or a combination thereof. The clonogenic potential of those cells can be assessed in the presence or absence of the agent or combination of agents to assess the efficacy of such treatment (i.e., for disrupting cancer stem cell survival and/or replication).

To the extent that the cancer stem cells are enriched from a mixed biopsy sample, then it is possible to use the results of these screening assays to identify in vitro, the most effective treatment regimen available for the cancer stem population enriched from primary tumor biopsies. This will allow for the identification of the most effective treatment regimen for a particular patient.

To assess the ability of one or more agents to modify cell differentiation, the cells can be in situ using appropriate stains for cell surface markers or genetic profiling using RT-PCR to assess whether cells grown in the presence of the one or more agents express a different marker or gene as compared to cells grown in the absence of the one or more agents. Alternatively cells can be removed from the microbubble wells using standard micromanipulation and microcapillary technology. Recovered cells can then be expanded in standard culture for further characterization studies.

EXAMPLES

The examples below are intended to exemplify the practice of the present invention but are by no means intended to limit the scope thereof.

Materials and Methods for Example 1-8

Cell Lines and Culture Conditions:
WM115 cell line, a tumorigenic human melanoma cell line, was cultured at 37° C. with 5% $CO_2$ in Eagle's Minimum Essential Medium (EMEM) (Lonza 12-611F) supplemented with 10% heat inactivated fetal bovine serum (FBS) (Gibco 10082-147, Invitrogen Corp., USA), 1% penicillin/streptomycin (PS) (Gibco 15140-122, Invitrogen Corp., USA) and 1% sodium pyruvate (Gibco 11360-070, Invitrogen Corp., USA).

Casting PDMS in Multiwell Plate:
Dow Corning's Sylgard® 184 silicone elastomer kit was used in a 10:1 base to curing agent ratio (w/w) to cast PDMS in multiwell plates. The pre-polymer components were manually mixed with a pipette tip in a 50 mL tube for 30 seconds and 300 µL of the PDMS pre-polymer was pipetted into each well of a 24-well plate and allowed to settle at room temperature for 30 min. The plates were then cured at 40° C. for 4 hours. For cell viability assays conducted on cells growing on PDMS, 50 µL of PDMS pre-polymer was pipetted into each well of a 96-well plate and cured at 40° C. for 24 hours. After curing PDMS in multiwell plates, the wells were individually rinsed with ethanol and stored at 40° C. until use.

Generation of NA/S and AM Sub-Populations:
WM115 cells were trypsinized from a confluent T-25 cell culture flask and plated ($2 \times 10^4$ cells/$cm^2$) on planar PDMS and cultured in standard media as described in Section 2.1. After 3 days, cells proliferating as non-adherent 3D clusters on planar PDMS were harvested by pipetting the media, centrifuged and resuspended in cell dissociation buffer, and plated into standard plasma treated polystyrene TCP ($1 \times 10^4$ cells/$cm^2$) to segregate NA/S and AM sub-populations. The NA/S was removed by pipetting the media in and out, centrifuged and resuspended in fresh media and were plated in TCP ($1 \times 10^4$ cells/$cm^2$). The AM sub-population was trypsinized, centrifuged and sub-cultured in TCP ($1 \times 10^4$ cells/$cm^2$). The NA/S sub-population and the AM sub-population were sub-cultured every fourth day.

Cell Viability Assays:
Cell viability assays were conducted to evaluate growth rate of cells plated on planar PDMS compared to standard TCP. Cells were seeded at two different densities, $1 \times 10^4$ cells/$cm^2$ and $2 \times 10^4$ cells/$cm^2$, onto PDMS cast in 96-well plate and onto standard 96-well TCP. A standard colorimetric MTT assay was performed 3 days after culture in which 3-(4,5-Dimethylthiazol-2-yl)-2,5-diphenyltetrazolium bromide) (Chemicon (Millipore) CT0-A, USA), was used to detect mitochondrial activity using a Modulus II Multimode Microplate Reader (Turner BioSystems). Staining experiments were also performed using calcein-AM (C3100MP, Invitrogen Corp., USA) and propidium iodide (PI) (P3566, Invitrogen Corp., USA) at 1.0 µM and 1.5 µM, respectively. For cells cultured on planar PDMS, cell culture media was carefully removed from the 96-well plate without removing non-adherent cells and then 100 µL of fresh media containing calcein-AM and PI was added and incubated in the dark for 30 min and imaged using a fluorescent microscope. Wash steps were not utilized to limit loss of nonadherent cells. Fluorescent images were taken using a fluorescent microscope (Olympus IX70-S8F) and analyzed using ImageJ (NIH, USA).

Flow Cytometry Analysis:
The expression levels of CD20 and CD271 were investigated on the parental WM115 cells propagating as a monolayer on TCP, the NA/S sub-population on TCP, the AM sub-population on TCP, and the NA/S seeded back onto PDMS propagating as non-distinct 3D clusters. To prepare the NA/S sub-population propagating with a non-distinct 3D clustered morphology on PDMS for flow cytometry analysis, the media was pooled together from 6 wells of a 24-well TCP cured with PDMS. The cells were loosely adhered to the planar PDMS surface and collecting the media ensured the removal of all the cells. The enriched NA/S cell sub-population on TCP was similarly harvested simply by collecting the media. The collected media in both cases was centrifuged and the resulting cell pellets were re-suspended in trypsin-EDTA (Gibco 25200-056, Invitrogen Corp., USA). This was done for consistency in sample processing with the AM sub-population and also to ensure that the cell surface markers were not affected by trypsin treatment. Equivalent amount of FBS was added to both cell sub-populations after 10 minutes of incubation in trypsin. The cells were centrifuged again and the pellets were resuspended with cell dissociation buffer (Gibco 13150-016, Invitrogen Corp., USA) to ensure complete dissociation of cell aggregates before incubating them with fluorochrome conjugated antibodies. The cell samples were then centrifuged and resuspended in 300 µL of staining buffer composed of 1% bovine serum albumin (BSA) (Hyclone SH30574.01, Thermo Scientific, USA), 0.1% sodium azide (SX0300, EM Science, USA) in 1× phosphate buffer saline (PBS) (BP13351 Fisher BioReagents, USA) and fluorochrome conjugated antibodies described below.

Cells propagating as a monolayer on TCP were trypsinized, centrifuged and resuspended in cell dissociation buffer. This was done to ensure a fair comparison between NA/S cells cultured on PDMS and TCP. The cell samples were then centrifuged and resuspended in 300 µL of staining buffer containing FITC mouse anti-human CD20 (BD Pharmingen 555622) and Alexa fluor 647 mouse anti-human CD271 (BD Pharmingen 560326). Each sample was incubated for 60 minutes in the dark at room temperature at a recommended volume per test (20 µL of antibody solution for $1 \times 10^6$ cells per sample). The appropriate single stain compensation controls were prepared for each of the antibodies. To adjust for non-specific binding of antibody to the cells, isotype controls were also used. FITC mouse IgG2b κ isotype control (BD Pharmingen 555742) and Alexa fluor 647 mouse IgG2b κ isotype control (BD Pharmingen 557714) were used at the same concentration as the antibody of interest. Each sample was then washed with PBS, centrifuged and resuspended in 3% formalin (VWR International) for analysis. The samples were analyzed using an 8-color BD FACSCanto II flow cytometer with filters for FITC (495 nm excitation/519 nm emission) and Alexa fluor 647 (640 nm excitation/668 nm emission). The results from flow cytometric analysis were analyzed using Flow-Jo v7.6 (Tree Star, Inc., USA) software.

Details of the gating process employed are illustrated in FIGS. 11A-E, where one representative example that was used on all the samples is shown. For each sample analyzed, appropriate controls were used. Unstained control, single stained (compensation) controls and isotype controls were analyzed for each of the samples. The FACSCanto II (BD Biosciences) has an internal auto-compensation program that was used to compensate for overlap in emission spectra.

The unstained control sample was first analyzed and the voltages for the filters were corrected for any auto fluorescence. The single stained (compensation) controls were then analyzed and the instrument was compensated for any overlap in emission spectra. FlowJo v7.6.1 (Tree Star Inc., USA) was used to analyze the samples. In brief, the scatter plot between FSC and SSC is a plot that gives a distribution of cells with respect to their relative size and granularity, respectively. From this plot, area pertaining to single cells was only selected, eliminating debris and multiple cell clusters. This was done on both isotype control sample and the compensated stained sample (FIGS. 11A-B). The fluorescent scatter plots were obtained for the gated cell population (FIGS. 11C-D). Quad-gate was used to quantify the percentage of cells expressing the surface markers under investigation. The quad-gate was placed in the isotype control so that all the cells are confined to the lower left quadrant which is negative for both the surface markers (FIG. 11C). In the stained sample, the quad-gate was placed at the same place as the isotype control (FIG. 11D). Thus, if the cells express a particular surface-marker the other quadrants gets populated with cells. There is a second level gating in the scatter plots to get the histograms for fluorescent intensity for each marker. The gated population in the scatter plots was further interrogated for their relative fluorescent intensity and an overlap of the relative intensity from the isotype control and the stained sample would give an estimate of the expression of that particular marker in the sample (FIG. 11E).

PDMS Microbubble Fabrication:

To fabricate microbubble arrays in PDMS, a silicon wafer mold layout was designed using AutoCAD® LT 2008 (Autodesk Inc., USA). The mold layout had 60 µm diameter circular shaped openings spaced 300 µm apart in 10×10 arrays. The silicon wafer was etched to 150 µm depth using the Bosch deep reactive ion etch (DRIE) process (Plasma Therm™ 770, MEMS and Nanotechnology Exchange LLC, Reston, Va.). The DRIE silicon wafer was received after the Bosch process with the resist layer intact. This wafer was used directly to mold PDMS microbubble arrays with the Dow Corning's Sylgard® 184 silicone elastomer kit in a 10:1 base to curing agent ratio (w/w). The pre-polymer components were manually mixed with a pipette tip in a 50 mL tube for 30 seconds and poured onto the silicon wafer mold. The mixture was allowed to self-level for 30 minutes at room temperature, and then rapidly cured at 100° C. for 2 hours. The cured PDMS with microbubbles was then peeled carefully and cut into small chips (1 cm×0.5 cm). Prior to use for cell culture experiments the chips were rinsed with ethanol, distilled water and blown dry with nitrogen. Typical chip thickness was 1 mm and each chip contained 405 microbubbles used for clonogenic potential measurements.

Clonogenic Potential Assay Using MB Arrays:

The NA/S and AM sub-populations of WM115 cell line generated were evaluated for their clonogenic potential using MB arrays formed in PDMS. The NA/S sub-population was collected from the cell culture dish by pipetting the media and then centrifuged. The resulting pellet was incubated in cell dissociation buffer (Gibco 13150-016, Invitrogen Corp., USA) for 20 minutes. The dissociated cells were centrifuged and re-suspended in cell culture media composed of Eagle's Minimum Essential Medium (EMEM) (Lonza 12-611F) supplemented with 10% heat inactivated fetal bovine serum (FBS) (Gibco 10082-147, Invitrogen Corp., USA), 1% penicillin/streptomycin (PS) (Gibco 15140-122, Invitrogen Corp., USA) and 1% sodium pyruvate (Gibco 11360-070, Invitrogen Corp., USA). The AM sub-population was trypsinized, centrifuged and the pellet re-suspended in cell culture media.

For cell culture experiments using PDMS microbubble arrays, small chips containing microbubbles, were rinsed with ethanol and distilled water and blown dry with nitrogen. Microbubble chips were placed in standard 24 well tissue culture plates (TCP) for cell culture experiments. To keep the chips submerged in the media during cell culture, the bottom side of the chips—opposite to the side with the microbubbles—was rendered hydrophilic by treating with atmospheric air plasma (March Plasmod®) for 10 min at 20 W. Once a chip was placed in the 24 well TCP, the top side of the chip was blocked with 50 µL of 1% bovine serum albumin (Hyclone™ SH30574.01, Thermo Scientific, USA) for 10 min. To replace the air trapped inside the microbubbles with cell culture media, the Vacuum-Assisted Coating (VAC) technique was utilized as previously described (Giang et al., "Microfabrication of Bubbular Cavities in PDMS for Cell Sorting and Microcell Culture Applications," *J Bionic Eng* 5(4):308e16 (2008), which is hereby incorporated by reference in its entirety). Briefly, 40 µL of sterile 1×PBS was pipetted onto the BSA blocked chips and the TCP with microbubble chips was placed in a desktop vacuum chamber for 30 min. A negative pressure (−690 mm Hg relative to atmospheric pressure) was applied to deplete the air trapped in the microbubbles, thereby allowing PBS to enter the microbubbles. A reagent exchange process was used to replace the PBS with cell culture media by removing most of the PBS with a pipette (being careful not to deprime the microbubbles) and 50 µL of cell culture media was placed on the top of microbubble chip.

Cell stock solution (50 µL, $4 \times 10^4$ cells/mL) was applied to the chip (A=0.5 cm$^2$) for 10 min at a seeding density of $4 \times 10^3$ cells/cm$^2$. After seeding, the cell solution was removed and the chip was rinsed twice by placing and removing 50 µL of media on the chip. This step was done to remove cells that may have deposited onto the planar surface of the microbubble chip. The chips were carefully transferred with forceps into a different well in a 24-well TCP filled with 1 mL of media. The 24-well plate containing the microbubble chips seeded with cells was then incubated at 37° C. and 5% $CO_2$. Culture media was changed every three days.

Statistical Analysis:

Unpaired Student's t-test was used when two separate sets of independent samples were compared to see if they were the same or different. This was done for comparing the MTT assay results for cells cultured on planar PDMS and TCP and median change in fluorescent intensity for surface marker expression to check if the change in expression was statistically significant. The Extreme Limiting Dilution Analysis (ELDA) tool (Hu and Smyth, "ELDA: Extreme Limiting Dilution Analysis for Comparing Depleted and Enriched Populations in Stem Cell and Other Assays," *J Immunol Methods* 347(1e2):70e8 (2009), which is hereby incorporated by reference in its entirety) with 95% confidence interval was used to determine the clonogenic potential of NA/S and AM sub-populations. The ELDA tool was designed based on single-hit Poisson model. ELDA is an established technique for single cell cloning of tumor initiating cells (Quintana et al., "Efficient Tumour Formation by Single Human Melanoma Cells," *Nature* 456(7222):593e8 (2008); Vaillant et al., "The Mammary Progenitor Marker CD61/beta3 Integrin Identifies Cancer Stem Cells in Mouse Models of Mammary Tumorigenesis," *Cancer Res* 68(19):7711e7 (2008); Vermeulen et al., "Single-cell Cloning of Colon Cancer Stem Cells Reveals a Multi-lineage Differentiation Capacity," *Proc Natl Acad Sci USA* 105(36):13427e32 (2008), each of which is hereby incorporated by reference in its entirety). Limiting dilution analysis assumes that the number of biologically active particles follows Poisson's distribution and one active cell is sufficient for a positive response from a culture (Moreau and Miller, "Growth at Limiting Dilution of Human T Cell Colonies from T Cell-depleted Peripheral Blood Leukocytes," *J Immunol* 130(3):1139e45 (1983), which is hereby incorporated by reference in its entirety). This study was done using three array chips with 1215 microbubble wells seeded with either 1, 2, or 3 cells per well for each of the two cell sub-populations.

Example 1

Morphology of WM115 Cell Line on Planar PDMS and TCP

WM115 cells were seeded at a density of $2 \times 10^4$ cells/cm$^2$ on TCP and planar PDMS and cultured as described in the preceding Materials and Methods. Results indicated that WM115 cells propagate as a monolayer on TCP (FIG. 3A); however, on planar hydrophobic PDMS they tend to propagate with a non-adherent 3D cluster morphology (FIG. 3B). Plasma treated TCP is hydrophilic, which favors cell adhesion and spreading, whereas PDMS is a hydrophobic polymer that hinders cell adhesion causing cells to adopt 3D cluster morphology.

Example 2

Viability of WM115 Cell Line on TCP and Planar PDMS

Cell viability was tested using an assay with calcein-AM and propidium iodide for live and dead stain, respectively. Calcein-AM is membrane permeable and is cleaved by active esterases in live cells which produce a fluorescence signal. Propidium iodide is cell membrane impermeable, however, dead cells that have degraded cell membranes allow the stain to enter where it intercalates DNA. The stains were applied to the cells after 4 days of incubation on planar PDMS and TCP (FIGS. 4A, 4D) as described in Section 2.4 and results showed that most cells were viable based on fluorescence visualization. Cells propagating as 3D clusters and monolayer on TCP stain positive for the live stain (FIGS. 4B, 4E) and there is very little staining for dead stain (FIGS. 4C, 4F). This suggested that there was sufficient nutrient uptake by cells propagating as 3D clusters on planar PDMS.

MTT assay results show the effect of the PDMS substrate on cell proliferation relative to TCP (FIG. 4G). The yellow MTT dye is reduced by mitochondrial reductase enzymes to form purple formazan crystals that can be dissolved and quantified by absorbance measurement which provides an indirect measure of cell viability based on metabolic activity. Unpaired Student t-test revealed that there was no significant difference (p>0.1) in metabolic activity between cells propagating as 3D clusters on planar PDMS and monolayer on TCP.

Example 3

Effect of Sub-Culturing WM115 Cell Line from Planar PDMS to TCP

WM115 cells propagating as 3D clusters on planar PDMS were non-adherent to the underlying substrate and pipetting the media ensured the removal of cells from the well. When the cells cultured on planar PDMS were harvested, dissociated and plated (seeding density=$1 \times 10^4$ cells/cm$^2$) as individual cells on TCP (FIG. 5A), cells with two distinct morphology emerged on TCP by the end of day 4 (FIG. 5B). WM115 cells exhibited a unique "fried egg" morphology comprised of cells that formed tightly packed non-adherent spheroids (NA/S) in the center surrounded by cells that propagated as an adherent monolayer (AM).

Example 4

Sub-Culturing the NA/S and AM Sub-Populations of the WM115 Cell Line

The cells in the NA/S sub-population (FIG. 5B) were loosely adhered to the TCP and pipetting the media facilitated their removal. Two representative images before and after the removal of NA/S sub-population are shown in FIGS. 12A-B. After removal of the NA/S cells the remaining AM sub-population was incubated with media for 24 hours to see if the AM cells were able to regenerate a NA/S sub-population. Results indicated that AM cells were not able to produce NA/S but they rather fill the space left behind by the spheroid cells after 24 hours (FIGS. 12C-D). The media containing the NA/S cells was centrifuged and the resulting pellets were dissociated, resuspended in media and replated (seeding density=$1\times10^4$ cells/cm$^2$) back onto TCP (FIGS. 6A, B). Results indicated that 24 hours after subculture, these cells formed NA/S (FIG. 6C). After removal of the NA/S cells the AM cells (FIG. 6D) were trypsinized, centrifuged, re-suspended in media and plated (seeding density=$1\times10^4$ cells/cm$^2$) back onto TCP (FIG. 6E). These cells only formed AM cells 24 hours after sub-culture (FIG. 6F). Thus, it was possible to propagate the NA/S and AM sub-populations separately on TCP.

Example 5

Effects of Passaging the NA/S and AM Sub-Populations of WM115 Cell Line on TCP

When the NA/S sub-population was passed on TCP, the presence of both NA/S sub-population and AM sub-population were observed. This was evident from the observation made four days after the first sub-culture step from PDMS which produced cells exhibiting the "fried egg" morphology with NA/S in the center surrounded by AM cells (FIG. 7A). Successive passaging of the NA/S cells on TCP (every fourth day) resulted in the progressive decrease of AM cells (FIGS. 7B-D). By the end of passage 4, there was an enriched NA/S sub-population on TCP (FIG. 7D) with very little incidence of AM cells around the NA/S and in the culture. Successively passaging the AM cells resulted in the enrichment of cells that retained the ability to propagate as a monolayer only (FIGS. 13A-B).

Example 6

Expression of CD20 and CD271 Stem-Cell Markers

To quantitate the presence of CSCs the expression of CD20 and CD271 stem cell markers were measured at several stages during the enrichment process including the parental line and the enriched NA/S and AM sub-populations. FIG. 8 schematically depicts the enrichment process and the stages at which cells were probed for CD20 and CD271 expression. In addition, the enriched NA/S cell sub-population was evaluated after culturing back onto PDMS. In this case, the NA/S cells were collected from the TCP, dissociated, and seeded on planar PDMS (seeding density=$2\times10^4$ cells/cm$^2$) and cultured for 3 days. FIGS. 9A-H indicate that the morphology and surface marker phenotype of WM115 cells vary at different stages (marked 1, 2, 3 and 4 in FIG. 8). The parental WM115 cell line propagated as a monolayer on TCP (FIG. 9A) and had 0.150% of CD20+CD271+ cells (FIG. 9B). The NA/S sub-population on TCP growing as tight spheroids (FIG. 9C) had 2.32% of CD20+CD271+ sub-population (FIG. 9D) and the AM sub-population (FIG. 9E) had 0.272% of CD20+CD271+ sub-population (FIG. 9F). Interestingly, only 34% of the cells in the AM sub-population were CD271+ cells compared to 61.8% of the cells in the parental WM115 cell line were CD271+; despite the fact that both were morphologically similar, propagating as a monolayer on TCP (FIG. 9A, 9E). When the NA/S cells were dissociated and seeded on planar PDMS they propagated as non-distinct 3D clusters (FIG. 9G) in contrast to the compact spheroid observed on TCP (FIG. 9C). Interesting, the emergence of a distinct population of CD20+CD271+ cells comprising 14.7% of sub-population was observed (FIG. 9H). The NA/S cell subpopulation propagating on planar PDMS also had a 1.73% CD20+ only sub-population which was ~100 fold higher than all the other samples (FIG. 9H). The change in expression levels of CD20 and CD271 in NA/S sub-population on planar PDMS with respect to parental WM115 cell line is quantified in FIGS. 14A-H. In brief, there is a statistically significant ~2.1 and ~1.8 fold change in the expression of CD20 ($p<0.05$) and CD271 ($p<0.01$), respectively (see FIGS. 14G-H).

Example 7

Fate of NA/S and AM Sub-Populations of WM115 Cell Line in Microbubble Arrays

Microbubble arrays (3 chips, 1215 wells total) were seeded with cells from the NA/S and AM sub-populations under limiting dilutions with the goal to seed one cell from each sub-population per microbubble well. On average the seeding protocol described in the preceding Materials & Methods produced a high total cell seeding efficiency (61.5%±7.7%) with the remainder of microbubble wells being empty. On average the single, two, and three cell seeding efficiencies were 31.1%±8.0%, 12.8%±1.0%, and 12.7%±4.4%, respectively. Metrics for defining the seeding efficiencies for the NA/S and AM arrays are provided in Table 1 below. The microbubble wells seeded with NA/S and AM sub-populations were inspected for the ability of cells to survive and proliferate.

TABLE 1

Metrics defining MB seeding efficiency NA/S sub-population and AM sub-population

| | | Values | |
|---|---|---|---|
| Parameter | Description | NA/S Sub-population | AM Sub-population |
| Total number of MB | No. of MB included in the study | 1215 | 1215 |
| MB seeding efficiency | No. of MB seeded/ Total No. of MB | 56.05% | 66.90% |
| Single cell seeding efficiency | No. of MB seeded with one cell/ Total No. of MB | 45.37% | 54.98% |
| Two cell seeding efficiency | No. of MB seeded with two cells/ Total No. of MB | 20.29% | 21.58% |

After seeding the wells were manually inspected and images were taken. After 5 days in culture the arrays were reinspected. Microbubbles that cells were observed to proliferate were scored positive. If there was no sign of proliferation the microbubble was scored negative. One representative image within the microbubble array chip immediately after seeding with cells from the NA/S sub-population is shown in FIG. 10A. The same area was imaged after five days (FIG. 10B). A positive culture is indicated by white arrow and a negative culture by black arrow. Representative images within the microbubble array chip immediately after seeding with cells from the AM sub-population and five days after seeding are shown in FIG. 10C and FIG. 10D, respectively.

Results indicate that in general microbubbles seeded with single cells from the AM sub-population are less likely to thrive, showing fewer signs of cellular activity. Positive cultures after 5 days are more common for microbubbles seeded with cells from the NA/S sub-population. Table 2 (below) indicates the percentage of microbubble wells showing positive culture for microbubbles with 1, 2, 3 and more than 3 cells per MB well. On an average ~57% of microbubbles seeded with single cells from the NA/S sub-population showed positive culture, whereas only ~7% of microbubbles seeded with single cells from the AM sub-population were able to survive and proliferate. There also was a stark difference for microbubbles seeded with 2 cells with ~80% and ~56% of microbubbles showing positive culture for NA/S and AM sub-populations, respectively. The ability to survive was nearly equal (~95% for NA/S sub-population and ~97% for adherent sub-population) for microbubbles seeded with 3 cells and there was no difference in survival characteristics for microbubbles seeded with more than 3 cells with all showing positive culture (100% survival) for both NA/S and AM sub-populations.

TABLE 2

Percentage of Microbubbles Showing Positive Culture by the end of Day 5 Seeded Under Limiting Dilution Conditions with Cells from NA/S and AM Sub-populations

| | Percentage of Positive Culture | | | |
|---|---|---|---|---|
| NA/S sub-population | 96.63 | 79.99 | 95.31 | 100 |
| AM sub-population | 7.16 | 56.36 | 97.43 | 100 |
| No. of cells per microbubble | 1 | 2 | 3 | >3 |

Example 8

Clonogenic Potential of NA/S and AM Sub-Populations

The online tool for computing limiting dilution problem (available from the Bioinformatics Division at the Walter and Eliza Hall Institute of Medical Research, Australia) was used to determine the clonogenic potential of NA/S and AM sub-populations (Giang et al., "Microfabrication of Bubbular Cavities in PDMS for Cell Sorting and Microcell Culture Applications," *J Bionic Eng* 5(4):308e16 (2008), which is hereby incorporated by reference in its entirety). It is especially suitable for analyzing limiting dilution data arising in stem cell research. ELDA can compare multiple groups or treatment conditions. By default, ELDA computes a 95% confidence for the active cell frequency in each population group. The data that is fed into the online computational tool and the results generated are summarized in Table 3 below. Briefly, "dose" refers to the number of cells in each MB; "tested" refers to the number of MB tested; "response" refers to the number of MB showing positive cultures, where positive is defined as a well seeded with 1-3 cells where cell proliferation was observed; and "group" refers to the sub-population used for seeding, NA/S or AM.

TABLE 3

Data input for Extreme Limiting Dilution Analysis

| Dose | Tested | Response | Group |
|---|---|---|---|
| 1 | 309 | 175 | NA/S |
| 2 | 147 | 117 | NA/S |

TABLE 3-continued

Data input for Extreme Limiting Dilution Analysis

| Dose | Tested | Response | Group |
|---|---|---|---|
| 3 | 192 | 183 | NA/S |
| 1 | 447 | 32 | AM |
| 2 | 165 | 93 | AM |
| 3 | 117 | 114 | AM |

ELDA tool estimated that cells from NA/S sub-population have a 1/1.72 (~58%) frequency to give rise to a clone (95% CI 1.62 to 1.84), whereas cells from the AM population have a 1/3.93 (~25%) frequency to give rise to a clone (95% CI 4.38 to 3.53). This frequency difference is statistically different ($p=4.41 \times 10^{-40}$) confirming that the NA/S cell subpopulations have a higher clonogenic potential, which is consistent with the higher percent of cells expressing stem cell markers.

Discussion of Examples 1-8

In vitro cell-substrate interactions are influenced by cell type and the material properties of the substrate. Electrostatic interactions allow cells to bind more strongly to oxidized charged surfaces (e.g. TCP) compared to neutrally charged surfaces such as PDMS (Seo et al., "Cell Adhesion on Phase-separated Surface of Block Copolymer Composed of Poly(2-methacryloyloxyethyl phosphorylcholine) and Poly(dimethylsiloxane)," *Biomaterials* 30(29):5330e40 (2009), which is hereby incorporated by reference in its entirety). The attachment of a cell to an artificial substrate also depends on protein adsorption. The optimum deposition of ECM proteins synthesized by the cell depends on the affinity of the secreted protein to adhere to the substrate (Groth and Altankov, "Fibroblast Spreading and Proliferation on Hydrophilic and Hydrophobic Surfaces Is Related to Tyrosine Phosphorylation in Focal Contacts," *J Biomater Sci Polym Ed* 7(3):297e305 (1995), which is hereby incorporated by reference in its entirety). The diminished ability of cells to spread on hydrophobic surface is attributed to the inability of cells to deposit ECM proteins (Keselowsky et al., "Surface Chemistry Modulates Focal Adhesion Composition and Signaling Through Changes in Integrin Binding," *Biomaterials* 25(28): 5947e54 (2004); Arima and Iwata, "Effect of Wettability and Surface Functional Groups on Protein Adsorption and Cell Adhesion Using Well-defined Mixed Selfassembled Monolayers," *Biomaterials* 28(20):3074e82 (2007); Sastry and Burridge, "Focal Adhesions: A Nexus for Intracellular Signaling and Cytoskeletal Dynamics," *Exp Cell Res* 261(1): 25e36 (2000); Garcia and Boettiger, "Integrin-fibronectin Interactions at the Cell-material Interface: Initial Integrin Binding and Signaling," *Biomaterials* 20(23e24):2427e33 (1999), each of which is hereby incorporated by reference in its entirety). To exemplify this point, fibronectin deposition and eventual cell attachment was higher on plasma treated hydrophilic PDMS as opposed to untreated hydrophobic PDMS (et al., "Fibronectin Adsorption on Surface-activated Poly(dimethylsiloxane) and Its Effect on Cellular Function," *J Biomed Mater Res A* 71(3):449e61 (2004), which is hereby incorporated by reference in its entirety). The substrate stiffness is also known have a profound effect in directing cell colony morphology (Yeung et al., "Effects of Substrate Stiffness on Cell Morphology, Cytoskeletal Structure, and Adhesion," *Cell Motil Cytoskeleton* 60(1):24e34 (2005), which is hereby incorporated by reference in its entirety). When cultured on soft substrates, fibroblasts assume a more rounded morphology, which is due to mechanical signaling that induces cells to form cell-cell contacts to survive (Yeung et al., "Effects of Substrate Stiffness on Cell Morphology, Cytoskeletal Structure, and Adhesion," *Cell Motil Cytoskeleton* 60(1):24e34 (2005), which is hereby incorporated by reference in its entirety). In summary, the hydrophobicity of PDMS combined with its lower modulus of elasticity and fairly neutral surface charge encourages cells to propagate as non-adherent clusters instead of spreading out as a monolayer on TCP (FIGS. 3A-B).

Recent studies suggest that a specific cell sub-population in melanoma may be the key driver of continuous heterogeneous tumor growth and metastasis (Held et al., "Characterization of Melanoma Cells Capable of Propagating Tumors from a Single Cell," *Cancer Res* 70(1):388e97 (2010); Fang et al., "A Tumorigenic Subpopulation with Stem Cell Properties in Melanomas," *Cancer Res* 65(20):9328e37 (2005); Schatton et al., "Identification of Cells Initiating Human Melanomas," *Nature* 451(7176):345e9 (2008); Monzani et al., "Melanoma Contains CD133 and ABCG2 Positive Cells with Enhanced Tumourigenic Potential," *Eur J Cancer* 43(5): 935e46 (2007); Ramgolam et al., "Melanoma Spheroids Grown under Neural Crest Cell Conditions Are Highly Plastic Migratory/invasive Tumor Cells Endowed with Immunomodulator Function," *PLoS ONE* 6(4):e18784 (2011); Perego et al., "Heterogeneous Phenotype of Human Melanoma Cells with in vitro and in vivo Features of Tumor-initiating Cells," *J Invest Dermatol* 130(7):1877e86 (2010); Civenni et al., "Human CD271-positive Melanoma Stem Cells Associated with Metastasis Establish Tumor Heterogeneity and Long-term Growth," *Cancer Res* 71(8):3098e109 (2011); Grichnik et al., "Melanoma, a Tumor Based on a Mutant Stem Cell?" *J Invest Dermatol* 126(1):142e53 (2006); Klein et al., "Increased Expression of Stem Cell Markers in Malignant Melanoma," *Mod Pathol* 20(1):102e7 (2007); Roesch et al., "A Temporarily Distinct Subpopulation of Slow-cycling Melanoma Cells is Required for Continuous Tumor Growth," *Cell* 141(4):583e94 (2010), each of which is hereby incorporated by reference in its entirety). This sub-population is thought to express many stem cell markers and these cancer stem cells are bestowed with the property of self-renewal and differentiation. The CSC sub-population has been characterized by studying the expression of surface markers using flow cytometry (Perego et al., "Heterogeneous Phenotype of Human Melanoma Cells with in vitro and in vivo Features of Tumor-initiating Cells," *J Invest Dermatol* 130(7):1877e86 (2010); Quintana et al., "Phenotypic Heterogeneity Among Tumorigenic Melanoma Cells from Patients that Is Reversible and not Hierarchically Organized," *Cancer Cell* 18:510e23 (2010); Civenni et al., "Human CD271-positive Melanoma Stem Cells Associated with Metastasis Establish Tumor Heterogeneity and Long-term Growth," *Cancer Res* 71(8):3098e109 (2011), each of which is hereby incorporated by reference in its entirety), the ability to efflux Hoeschst dye (Grichnik et al., "Melanoma, a Tumor Based on a Mutant Stem Cell?" *J Invest Dermatol* 126(1):142e53 (2006), which is hereby incorporated by reference in its entirety), and by assessing their ability to form spheroids (Fang et al., "A Tumorigenic Subpopulation with Stem Cell Properties in Melanomas," *Cancer Res* 65(20):9328e37 (2005); Ramgolam et al., "Melanoma Spheroids Grown under Neural Crest Cell Conditions Are Highly Plastic Migratory/invasive Tumor Cells Endowed with Immunomodulator Function," *PLoS ONE* 6(4):e18784 (2011); Perego et al., "Heterogeneous Phenotype of Human Melanoma Cells with in vitro and in vivo Features of Tumor-initiating Cells," *J Invest Dermatol* 130(7):1877e86 (2010), each of which is hereby incorporated by reference in its entirety). Fundamental differences in growth rate, morphology, and anchorage independent survival between the CSC sub-population and the bulk tumor cells are exploited to identify the aggressive tumor initiating cells (Fang et al., "A Tumorigenic Subpopulation with Stem Cell Properties in Melanomas," *Cancer Res* 65(20):9328e37 (2005); Lin and Chang, "Recent Advances in Three-dimensional Multicellular Spheroid Culture for Biomedical Research," *Biotechnol J* 3(9e10):1172e84 (2008); Yamada and Cukierman, "Modeling Tissue Morphogenesis and Cancer in 3D," *Cell* 130(4):601e10 (2007), each of which is hereby incorporated by reference in its entirety). This has led to spheroid cell culture as a popular method for enriching CSCs from solid tumors (Ramgolam et al., "Melanoma Spheroids Grown under Neural Crest Cell Conditions Are Highly Plastic Migratory/invasive Tumor Cells Endowed with Immunomodulator Function," *PLoS ONE* 6(4):e18784 (2011); Perego et al., "Spheres of Influence in Cancer Stem Cell Biology," *J Invest Dermatol* 131(2):546e7 (2011), each of which is hereby incorporated by reference in its entirety). However, there is great variation in the number of cells endowed with stem-like features in surgical samples. This combined with the relative impurity of cells from primary tumors and the difficulty associated with in vitro maintenance of primary cells have resulted in several research groups attempting to exploit the relative heterogeneity and ease of maintenance of established melanoma cell lines for CSC research. For example, the WM115 and WM-266-4 tumorigenic melanoma cell lines isolated from primary and metastatic melanoma lesions from the same patient by the Meenhard Herlyn's laboratory at the Wistar Institute, are extensively being exploited for CSC studies (Fang et al., "A Tumorigenic Subpopulation with Stem Cell Properties in Melanomas," *Cancer Res* 65(20):9328e37 (2005); Monzani et al., "Melanoma Contains CD133 and ABCG2 Positive Cells with Enhanced Tumourigenic Potential," *Eur J Cancer* 43(5):935e46 (2007); Na et al., "Isolation and Characterization of Spheroid Cells from Human Malignant Melanoma Cell Line WM-266-4," *Tumour Biol* 30(5e6):300e9 (2009), each of which is hereby incorporated by reference in its entirety).

In the preceding Examples, a simple in vitro method for enriching cells propagating as nonadherent/spheroids was performed by sub-culturing cells from TCP to PDMS and back onto TCP. WM115 cells sub-cultured from PDMS back to TCP spontaneously assemble into two distinct sub-populations consisting of cells exhibiting a distinct tightly packed NA/S morphology surrounded by AM cells (FIGS. 4A-G). The NA/S cells were sub-cultured by removing the media (FIGS. 5A-B) and subsequently passaged on hydrophilic TCP to select out the AM sub-population (FIGS. 6A-F). The AM cells were sub-cultured by trypsinizing and passaging them on hydrophilic TCP (FIGS. 5A-B). This process resulted in the propagation of cells that retained only the ability to grow as a monolayer (FIGS. 13A-B). This in vitro method does not require use of complex stem cell media and enables enrichment of the NA/S forming cell sub-population within a few days. The NA/S sub-population is not clonally pure as would be generated in the time consuming limiting dilution assay but selecting out the adherent fraction provides an enriched sub-population that constitutes a unique starting point for identifying CSC, generating clonal pure samples, and tumorigenicity studies.

The surface markers chosen for characterizing the CSC phenotype of the NA/S and AM cell subpopulations generated from the WM115 cell line were based on literature (Fang et al., "A Tumorigenic Subpopulation with Stem Cell Properties in Melanomas," *Cancer Res* 65(20):9328e37 (2005);

Boiko et al., "Human Melanoma-initiating Cells Express Neural Crest Nerve Growth Factor Receptor CD271," *Nature* 466(7302):133e7 (2010); Monzani et al., "Melanoma Contains CD133 and ABCG2 Positive Cells with Enhanced Tumourigenic Potential," *Eur J Cancer* 43(5):935e46 (2007); Ramgolam et al., "Melanoma Spheroids Grown under Neural Crest Cell Conditions Are Highly Plastic Migratory/invasive Tumor Cells Endowed with Immunomodulator Function," *PLoS ONE* 6(4):e18784 (2011), which is hereby incorporated by reference in its entirety). Previous work showed that when the WM115 melanoma cells were cultured in normal media conditions they propagated only as adherent cells however, when cultured in human embryonic stem cell (hESC) media they proliferated as non-adherent spheres (Fang et al., "A Tumorigenic Subpopulation with Stem Cell Properties in Melanomas," Cancer Res 65(20):9328e37 (2005), which is hereby incorporated by reference in its entirety). These sphere forming cells were enriched in CD20+ population and were able to self-renew, undergo multi-lineage differentiation and had increased in vivo tumorigenicity in immunocompromised mice (Fang et al., "A Tumorigenic Subpopulation with Stem Cell Properties in Melanomas," Cancer Res 65(20): 9328e37 (2005), which is hereby incorporated by reference in its entirety). When MeWo melanoma cells were cultured as spheroids they also expressed CD20+ and were shown to lack certain differentiation markers in contrast to adherent cells (Schmidt et al., "Eradication of Melanomas by Targeted Elimination of a Minor Subset of Tumor Cells," *Proc Natl Acad Sci USA* 108(6):2474e9 (2011), which is hereby incorporated by reference in its entirety). Targeting the CD20+ cell population in MeWo melanoma tumors, that represented less than 2% of the cells, resulted in the eradication of tumors in immunocompromised mice (Schmidt et al., "Eradication of Melanomas by Targeted Elimination of a Minor Subset of Tumor Cells," *Proc Natl Acad Sci USA* 108(6):2474e9 (2011), which is hereby incorporated by reference in its entirety). Expression of CD271 has been found in a number of neural crest derived tissues including melanoma (Boiko et al., "Human Melanoma-initiating Cells Express Neural Crest Nerve Growth Factor Receptor CD271," *Nature* 466(7302): 133e7 (2010), which is hereby incorporated by reference in its entirety). Research by others, found CD271 to be expressed in ~2.5% to ~41% of the total cell population isolated from primary melanoma tumors (Boiko et al., "Human Melanoma-initiating Cells Express Neural Crest Nerve Growth Factor Receptor CD271," *Nature* 466(7302): 133e7 (2010), which is hereby incorporated by reference in its entirety). Xenotransplantion studies found the CD271+ melanoma cell population resulted in tumors at a markedly higher rate when compared to CD271-cells (Boiko et al., "Human Melanoma-initiating Cells Express Neural Crest Nerve Growth Factor Receptor CD271," *Nature* 466(7302): 133e7 (2010), which is hereby incorporated by reference in its entirety). The presence of CD271+ cells were found in melanoma spheroids produced by culturing cells on pHEMA coated TCP. These CD271+ cells were observed to play a critical role in tumor formation using animal models (Quintana et al., "Phenotypic Heterogeneity Among Tumorigenic Melanoma Cells from Patients that Is Reversible and not Hierarchically Organized," *Cancer Cell* 18:510e23 (2010), which is hereby incorporated by reference in its entirety). In summary, melanoma cells propagating as 3D spheroids tend to express higher levels of CD20 and CD271 and exhibit higher tumorigenicity. Therefore, the expression of these stem cell markers was investigated for the morphologically distinct NA/S and AM sub-populations. Flow cytometry revealed phenotypic differences with the constituent CD20+ CD271+ cells in the NA/S sub-population exhibiting a ~10× higher presence than in the AM sub-population (FIGS. 9D, F). When the NA/S sub-population was dissociated and seeded back onto planar PDMS they adopted a non-distinct 3D cluster morphology (FIG. 9G). This further enriched the constituent CD20+CD271+ cells to ~50× that of the AM-subpopulation (FIGS. 9H, F). Future studies will seek to validate the anticipated enhanced in vivo tumorigenicity of the NA/S subpopulation over the AM and parental WM115 cell lines.

Clonogenic potential is a common metric used to quantify the frequency of stem cell or tumor initiating cells in a heterogeneous sample. Clonogenic potential is defined as the ability of a single cell to generate daughter cells. If tumor progression and metastasis is driven by CSCs that can self-renew and differentiate, these cells must possess a privileged capacity to proliferate and therefore are expected to exhibit a higher clonogenic potential than the bulk tumor cells. Here, microbubble arrays were employed to determine the clonogenic potential of the enriched NA/S and AM sub-populations. In previous work it was demonstrated that microbubble wells can be used for viable cell culture applications (Giang et al., "Microfabrication of Bubbular Cavities in PDMS for Cell Sorting and Microcell Culture Applications," *J Bionic Eng* 5(4):308e16 (2008), which is hereby incorporated by reference in its entirety). The unique architecture of the microbubble well enables cells to rapidly condition their microenvironment by secreting factors that accumulate to bioactive levels (Chandrasekaran et al., "Microenvironment Induced Spheroid to Sheeting Transition of Immortalized Human Keratinocytes (HaCaT) Cultured in Microbubbles Formed in Polydimethylsiloxane," *Biomaterials* 32(29):7159e68 (2011), which is hereby incorporated by reference in its entirety). Indeed, in a microbubble based perfusion system for 3D culture of multi-cellular tumor spheroids, it was shown that tumor cells propagating in microbubbles were more resistant to doxorubicin treatment, resembling the actual disease condition (Agastin et al., "Continuously Perfused Microbubble Array for 3D Tumor Spheroid Model," *Biomicrofluidics* 5(2):024110 (2011), which is hereby incorporated by reference in its entirety). Thus, microbubbles have potential to comprise an in vitro platform with a close resemblance to in vivo conditions to interrogate the clonogenic potential of cells.

In general, plating 0.2 to 20 cells per µL is an accepted standard for cell growth under clonal conditions (Pastrana et al., "Eyes Wide Open: A Critical Review of Sphere-formation as an Assay for Stem Cells," *Cell Stem Cell* 8(5):486e98 (2011), which is hereby incorporated by reference in its entirety). Plating cells at the higher end of this range creates a more permissive culture condition but potentially trades off clonal purity (Pastrana et al., "Eyes Wide Open: A Critical Review of Sphere-formation as an Assay for Stem Cells," *Cell Stem Cell* 8(5):486e98 (2011), which is hereby incorporated by reference in its entirety). It is common, for example, to seed 1 cell in a 96-well plate, which equates to a stringent plating condition of 0.01 cells per µL (assuming a media volume of 100 µL per well) but ensures clonal purity. Typical microbubbles used in the experiments reported here, have diameters of ~160 µm and a volume of ~2 nL. Seeding 1 cell per microbubble well equates to a plating density of 500 cell per µL, neglecting media exchange with the bulk reservoir. The exceedingly small media volume per cell creates a highly permissive culture condition that allows for the concentration of soluble factors produced by the cell to rise to bioactive levels, thereby conditioning the local microenvironmental niche to influence its function. This property is exploited for determining the clonogenic potential of the NA/S and AM sub-populations of the WM115 cell line. The hypothesis behind using microbubble well arrays to determine the clonogenic potential is that, more aggressive cells with tumor initiating capability will exhibit a privileged capacity to survive and therefore will be able to condition the microenvironment to survive and proliferate in the microbubble. It is important to note here that the stringency of the test can be altered by changing the microbubble size or number of cells seeded per well, and/or coating the microbubble with ECM proteins in addition to the assay time. Here, uncoated, hydrophobic microbubble arrays with 1215 wells were seeded with 1, 2, 3, or >3 cells per microbubble well. After 5 days the numbers of microbubble wells showing positive culture were quantified. The results indicated that single cells from the NA/S sub-population had greater tendency to survive and proliferate in microbubbles compared to single cells from the AM sub-population (FIGS. 10A-D, Table 1). Differences in cell survival and proliferation capacity between the NA/S and AM sub-populations were negated however, when >3 cells were seeded per microbubble (Table 1); suggesting a decrease in the stringency of the microbubble assay with increased cell seeding. The ELDA web tool with 95% confidence interval was used to determine the clonogenic potential—defined as the percentage of cells within the sub-populations that can give rise to clones. Results for microbubbles seeded with 1, 2, and 3 cells per microbubble well were used as input. ELDA estimated that ~25% of the cells from AM sub-population and ~58% of the cells from the NA/S sub-population were capable of giving rise to clones. The difference in clonogenic potential was statistically significant ($\chi^2=176$, p=4.41e-40). These results are consistent with literature that suggests melanoma spheroid cells express higher levels of CD20 and CD271 and are more aggressiveness (Fang et al., "A Tumorigenic Subpopulation with Stem Cell Properties in Melanomas," *Cancer Res* 65(20):9328e37 (2005); Ramgolam et al., "Melanoma Spheroids Grown under Neural Crest Cell Conditions Are Highly Plastic Migratory/invasive Tumor Cells Endowed with Immunomodulator Function," *PLoS ONE* 6(4):e18784 (2011); Perego et al., "Heterogeneous Phenotype of Human Melanoma Cells with in vitro and in vivo Features of Tumor-initiating Cells," *J Invest Dermatol* 130 (7):1877e86 (2010), each of which is hereby incorporated by reference in its entirety). The observation that ~25% of cells in the AM sub-population can give rise to clones, thus exhibiting a privileged capacity to proliferate, is also consistent with in vivo xenotransplantation experiments that find adherent cells can give rise to tumors in mice (Perego et al., "Spheres of Influence in Cancer Stem Cell Biology," *J Invest Dermatol* 131(2):546e7 (2011); Schatton and Frank, "The in vitro Spheroid Melanoma Cell Culture Assay: Cues on Tumor Initiation?" *J Invest Dermatol* 130(7):1769e71 (2010), each of which is hereby incorporated by reference in its entirety). Upon recovery of clones of both sub-populations from the microbubble wells, it is also possible to use gene arrays and protein/mRNA expression profiling to discover the genes and proteins responsible for conferring the observed privilege capacity to proliferate.

Developing simple in vitro assays for enriching and characterizing CSCs can ultimately lead to the development of therapies that target them within solid tumors. In the preceding Examples, two simple and rapid assays were utilized to investigate the presence of CSC in the primary WM115 melanoma cell line. The first assay allowed the enrichment of morphologically distinct cells propagating as non-adherent spheroids and an adherent monolayer. The primary cells are first cultured on PDMS cast in 24 well TCP where they adopt a 3D cluster morphology. After 3 days cells are transferred back on to hydrophilic TCP where morphological distinct spheroid and adherent cell subpopulations arise. The hydrophobic and elastomeric properties of the PDMS contribute to development of these sub-populations. Culturing the WM115 NA/S cell subpopulation on planar PDMS resulted in a significant enrichment (~15%) of cells expressing CD20+ and CD271+ stem cell markers. The second assay utilized microbubble arrays to determine the clonogenic potential of the isolated NA/S and AM sub-populations. Microbubble arrays have the potential to closely mimic in vivo tumor-cell microenvironment. Quantifying the ability of the cells to survive and proliferate inside the microbubble arrays (positive culture) and analyzing results using the Extreme Limiting Dilution Analysis (ELDA) web tool, found that the cells from the NA/S sub-population had a higher clonogenic potential (~58%) as opposed to cells from the AM sub-population (~25%). The observations of increased expression of stem-cell markers and higher clonogenic potential of NA/S sub-population support existing literature, confirming the utility of spheroid cell cultures for enriching CSCs in melanoma. It is believed that these assays are broadly applicable to identify CSC, and establish a link between sphere formation and CSC presence.

The preceding Examples using the tumorigenic WM115 melanoma call line therefore demonstrate a simple, rapid and cost effective in vitro protocol to fractionate NA/S and AM sub-populations from a heterogeneous cell population, as well as the use of microbubble arrays as a platform for determining the in vitro clonogenic potential of different sub-populations. Stem-cell surface marker analysis confirmed enrichment of CSCs in the NA/S sub-population, which also exhibits a higher clonogenic potential than the AM sub-population. These findings add credibility to the notion of using in vitro spheroid cell culture for enriching CSCs in not only melanoma, but also other forms of cancer; and these formats will allow for their characterization and as well as the screening and development of therapies that target this rare sub-population of aggressive cancer cells.

Example 9

Figure 15:
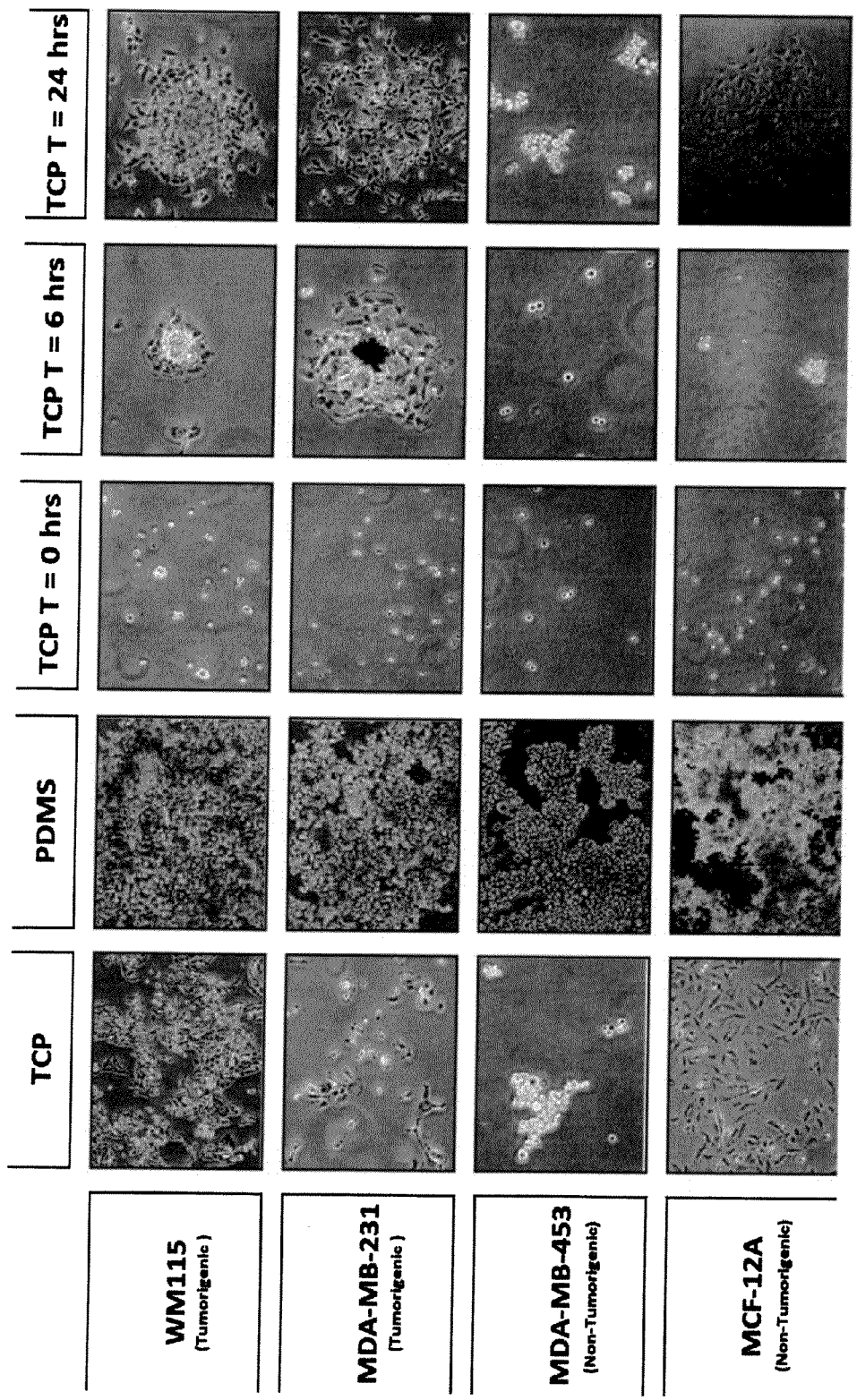
FIG. 15 contains a panel of images of three breast cell lines that vary in tumorigenicity taken at various time points during the in vitro enrichment assay, with the WM115 tumorigenic melanoma cell line repeated as a control. MDA-MB-231 is a tumorigenic cell line that was derived from a metastatic pleural lesion. MDA-MB-453 is a non-tumorigenic metastatic carcinoma cell line derived from a mammary gland. The MCF-12A is a nontumorigenic normal cell line derived from a mammary gland.

Enrichment of NA/S and AM Sub-Populations in Other Tumorigenic and Non-Tumorigenic Cell Lines Two tumorigenic cell lines, the WM115 melanoma (as used in Examples 1-8) and the MDA-MB-231 metastatic breast cell lines, both yielded two obvious distinct adherent and spheroid sub-populations from the parental line after being moved from PDMS to the TCP according to the in vitro enrichment assay described in Examples 1-5 (FIG. 15, first and second rows, respectively). Interestingly, the MDA-MB-231 sphere subpopulation on TCP was transient and within 24 hr cells appeared to revert back to adherent cells, suggesting modifications to the process depicted in FIG. 8 will be used to produce a stable spheroid subpopulation. Modifications include longer culture on PDMS, recovery of NA/S fraction from TCP for further subculture on PDMS, or both in combination (see FIG. 1). The presence of 3D spheroids from a tumorigenic line has been widely accepted as the confirmation that CSCs are present, which indicates that such cells may be present in the MDA-MB-231 cell line. The non-tumorigenic mammary gland metastatic carcinoma MDA-MB-453 cell line, which grows on TCP as loosely adhered cell clusters, showed no morphological difference after the in vitro enrichment assay had been performed (FIG. 15, third row). Results for the non-tumorigenic MDA-MB-453 are consistent with expectations as this cell line should not contain CSCs.

Unexpectedly, the immortalized normal mammary gland MCF-12A cell line did produce a transient spheroid subpopulation after the in vitro enrichment assay. Since it is a characteristic of stem cells with the capacity for multilineage differentiation, to be isolated on the basis of their poor adherence to TCP (Arsic et al., "Muscle-derived Stem Cells Isolated as Non-adherent Population Give Rise to Cardiac, Skeletal Muscle and Neural Lineages," *Exp Cell Res.* 314(6): 1266-80 (2008); Wan et al., "Nonadherent Cell Population of Human Marrow Culture is a Complementary Source of Mesenchymal Stem Cells (MSCs)," *J Orthop Res.* 24(1):21-8 (2006); Dontu et al., "In vitro Propagation and Transcriptional Profiling of Human Mammary Stem/Progenitor Cells," *Genes Dev.* 17(10):1253-70 (2003), each of which is hereby incorporated by reference in its entirety), this result indicates the usefulness of the in vitro enrichment process to derive somatic stem/progenitor cells from non-tumorigenic cell lines. The transient nature of the sphere subpopulation suggests a rapid differentiation process on TCP, and therefore the need for further subculture on PDMS to stabilize and/or reinforce establishment of the stem cell/progenitor phenotype.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of enriching cancer stem cells comprising:
   a first growing of a heterogeneous cell sample comprising cancer stem cells on a first substrate that is hydrophobic and has an elastic modulus less than about 100 MPa;
   a first recovering of the heterogeneous cell sample from the first substrate;
   a second growing of the recovered heterogeneous cell sample on a second substrate having an elastic modulus higher than the elastic modulus of the first substrate to produce a subpopulation of nonadherent cells and a subpopulation of adherent cells; and
   a second recovering of the nonadherent cell subpopulation from the second substrate, which is enriched for cancer stem cells.

2. The method according to claim 1, further comprising: repeating said second growing and said second recovering using the nonadherent cell subpopulation to obtain further enriched subpopulations of cancer stem cells.

3. The method according to claim 1, wherein the elastic modulus of the first substrate is about 100 Pa to about 50 MPa.

4. The method according to claim 1, wherein the elastic modulus of the first substrate is about 1 kPa to about 30 MPa.

5. The method according to claim 1, wherein the first substrate has a surface energy of less than about 30 dynes/cm, exhibits an air-water contact angle that is greater than about 80 degrees, or both.

6. The method according to claim 1, wherein the first substrate is a natural or synthetic rubber, a silicone, polydimethylsiloxane (PDMS), a low density poly(ethylene-covinyl acetate), a low density polyethylene, a low density polyurethane, fluorinated versions thereof, or copolymers thereof.

7. The method according to claim 1, wherein the second substrate has an elastic modulus of at least about 500 MPa.

8. The method according to claim 1, wherein the second substrate has a surface energy of greater than about 40 dynes/cm, exhibits an air-water contact angle that is less than about 50 degrees, or both.

9. The method according to claim 1, wherein the second substrate is glass or an oxygen plasma-treated polymer selected from the group consisting of polystyrene, polystyrene/acrylonitrile copolymers, high density polyurethane, high and medium density polyethylene, polyamide, polypropylene, and polyvinylchloride.

10. The method according to claim 1, wherein the first substrate is PDMS and the second substrate is polystyrene.

11. The method according to claim 1, wherein said first recovering is carried out by aspiration.

12. The method according to claim 1, wherein the enriched subpopulations are phenotypically distinct from the subpopulation of adherent cells.

* * * * *